US011858919B2

(12) United States Patent
Van Duzer et al.

(10) Patent No.: US 11,858,919 B2
(45) Date of Patent: Jan. 2, 2024

(54) HDAC1,2 INHIBITORS

(71) Applicant: REGENACY PHARMACEUTICALS, LLC, Waltham, MA (US)

(72) Inventors: John H. Van Duzer, Concord, MA (US); Ralph Mazitschek, Weston, MA (US); Charles Blum, Lexington, MA (US)

(73) Assignee: Regenacy Pharmaceuticals, Inc., Waltham, MA (US)

( * ) Notice: Subject to any disclaimer, the term of this patent is extended or adjusted under 35 U.S.C. 154(b) by 0 days.

(21) Appl. No.: 17/278,485

(22) PCT Filed: Sep. 25, 2019

(86) PCT No.: PCT/US2019/052913
§ 371 (c)(1),
(2) Date: Mar. 22, 2021

(87) PCT Pub. No.: WO2020/068950
PCT Pub. Date: Apr. 2, 2020

(65) Prior Publication Data
US 2022/0033388 A1 Feb. 3, 2022

Related U.S. Application Data

(60) Provisional application No. 62/736,281, filed on Sep. 25, 2018, provisional application No. 62/736,280, filed on Sep. 25, 2018.

(51) Int. Cl.
*C07D 409/12* (2006.01)
*C07D 209/34* (2006.01)
*C07D 235/08* (2006.01)

(52) U.S. Cl.
CPC ......... *C07D 409/12* (2013.01); *C07D 209/34* (2013.01); *C07D 235/08* (2013.01)

(58) Field of Classification Search
CPC ... C07D 409/12; C07D 209/34; C07D 235/08
See application file for complete search history.

(56) References Cited

U.S. PATENT DOCUMENTS

| | | | | |
|---|---|---|---|---|
| 7,868,205 | B2 * | 1/2011 | Moradei | C07D 257/04 |
| | | | | 544/379 |
| 8,168,658 | B2 | 5/2012 | Grimm et al. | |
| 8,598,168 | B2 | 12/2013 | Moradei et al. | |
| 9,145,412 | B2 | 9/2015 | van Duzer et al. | |
| 9,421,212 | B2 * | 8/2016 | van Duzer | C07D 215/54 |
| 10,774,056 | B2 * | 9/2020 | van Duzer | C07D 333/20 |
| 2014/0128391 | A1 * | 5/2014 | van Duzer | C07D 215/54 |
| | | | | 544/379 |
| 2016/0137630 | A1 * | 5/2016 | Shearstone | C07D 409/14 |
| | | | | 544/379 |
| 2016/0272579 | A1 | 9/2016 | Mazitschek et al. | |

FOREIGN PATENT DOCUMENTS

| | | | | |
|---|---|---|---|---|
| WO | WO-2005030705 A1 * | 4/2005 | | A61P 17/06 |
| WO | WO2007/118137 A1 * | 10/2007 | | |
| WO | WO2016/057779 A2 * | 4/2016 | | |
| WO | WO2017/136451 A1 * | 8/2017 | | |

OTHER PUBLICATIONS

International Preliminary Report on Patentability for PCT/US2019/052913 dated Mar. 23, 2021, 5 pages.
International Search Report for PCT/US2019/052913 dated Dec. 10, 2019, 3 pages.

* cited by examiner

*Primary Examiner* — Shawquia Jackson
(74) *Attorney, Agent, or Firm* — Brian C. Trinque; Nicole Sassu; Lathrop GPM LLP

(57) ABSTRACT

Provided herein are compounds, pharmaceutical compositions comprising such compounds, and methods of using such compounds to treat diseases or disorders associated with HDAC1 and/or HDAC2 activity.

16 Claims, No Drawings

HDAC1,2 INHIBITORS

RELATED APPLICATIONS

This application claims priority to U.S. Provisional Application No. 62/736,280 filed on Sep. 25, 2018, and U.S. Provisional Application No. 62/736,281 filed on Sep. 25, 2018, the contents of which are incorporated in their entirety.

BACKGROUND

A biological target of interest is histone deacetylase (HDAC) (see, for example, a discussion of the use of inhibitors of histone deacetylases for the treatment of cancer: Marks et al. *Nature Reviews Cancer* 2001, 7, 194; Johnstone et al. *Nature Reviews Drug Discovery* 2002, 287). Post-translational modification of proteins through acetylation and deacetylation of lysine residues plays a critical role in regulating their cellular functions. HDACs are zinc hydrolases that modulate gene expression through deacetylation of the N-acetyl-lysine residues of histone proteins and other transcriptional regulators (Hassig et al. *Curr. Opin. Chem. Biol.* 1997, 1, 300-308). HDACs participate in cellular pathways that control cell shape and differentiation, and an HDAC inhibitor has been shown to be effective in treating an otherwise recalcitrant cancer (Warrell et al. *J. Natl. Cancer Inst.* 1998, 90, 1621-1625).

Eleven human HDACs, which use Zn as a cofactor, have been identified (Taunton et al. *Science* 1996, 272, 408-411; Yang et al. *J. Biol. Chem.* 1997, 272, 28001-28007. Grozinger et al. *Proc. Natl. Acad. Sci. U.S.A.* 1999, 96, 4868-4873; Kao et al. *Genes Dev.* 2000, 14, 55-66. Hu et al. *J. Biol. Chem.* 2000, 275, 15254-15264; Zhou et al. *Proc. Natl. Acad. Sci U.S.A.* 2001, 98, 10572-10577; Venter et al. *Science* 2001, 291, 1304-1351) and these members fall into three classes (class 1, 11, and IV) based on sequence homology to their yeast orthologues (O. Witt et al. *Cancer Letters,* 2009, 277, 8-21). Class I HDACs include HDAC1, HDAC2, HDAC3, and HDAC8, and are referred to as "classical" HDACs, which implies a catalytic pocket with a $Zn^{2+}$ ion at its base.

There remains a need for preparing structurally diverse HDAC inhibitors, particularly ones that are potent and/or selective inhibitors of particular classes of HDACs and individual HDACs.

SUMMARY

Provided herein are compounds and methods of using these compounds to treat disorders related to HDAC1 or HDAC2 function, including cancer, myelodysplastic syndrome, and hemoglobinopathy.

In an aspect, provided herein are compounds of Formula I:

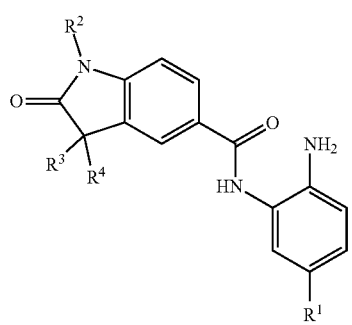

(I)

or a pharmaceutically acceptable salt thereof;

wherein:
$R^1$ is selected from the group consisting of aryl, aryl-OH, and heteroaryl;
$R^2$ is selected from the group consisting of —H, methyl, alkyl-cycloalkyl, and alkyl-heterocycloalkyl; and
$R^3$ and $R^4$ are independently, at each occurrence, selected from the group consisting of —H, halo, and methyl.

In another aspect, provided herein are compounds of Formula II:

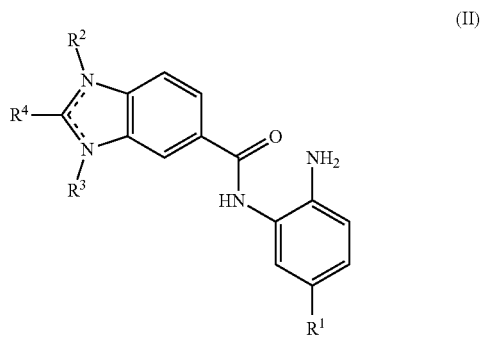

(II)

or a pharmaceutically acceptable salt thereof;
wherein:
$R^1$ is selected from the group consisting of aryl and heteroaryl;
$R^2$ is selected from the group consisting of absent, —H, methyl, and alkyl-heterocycloalkyl;
$R^3$ is selected from the group consisting of absent, —H, and alkyl-heterocycloalkyl;
$R^4$ is selected from the group consisting of —H, —OH, cycloalkyl, and methyl; and
===== indicates and optionally double bond.

In yet another aspect, provided herein is a compound of Formula III:

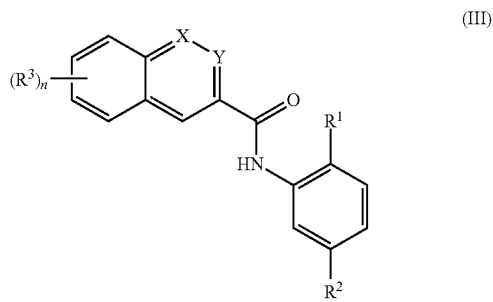

(III)

or a pharmaceutically acceptable salt thereof;
wherein:
X and Y are independently, at each occurrence, selected from the group consisting of CH and N, provided at least one of X and Y are N;
$R^1$ is selected from the group consisting of —N($R^4$)$_2$ and —OR$^4$;
$R^2$ is selected from the group consisting of halo, aryl, and heteroaryl; wherein aryl or heteroaryl are optionally substituted by one or more $R^5$ groups;
$R^3$ is independently, at each occurrence, selected from the group consisting of halo, cycloalkyl, heterocycloalkyl, —N($R^6$)—$C_1$-$C_3$ alkyl-N($R^6$)$_2$, —O—$C_1$-$C_3$ alkyl-N($R^6$)$_2$, and —N(R$^6$)—C$_1$-C$_3$ alkyl-OR$^6$; wherein cycloalkyl and heterocycloalkyl are optionally substituted by one or more R$^5$ groups;

R$^4$ is independently, at each occurrence, selected from the group consisting of —H, C$_1$-C$_6$ alkyl, and C$_1$-C$_6$ alkoxy;

R$^5$ is independently, at each occurrence, selected from the group consisting of —H and C$_1$-C$_6$ alkyl;

R$^6$ is independently, at each occurrence, selected from the group consisting of —H, C$_1$-C$_6$ alkyl, and C$_1$-C$_6$ alkoxy; and n is 0, 1, 2, or 3.

In an embodiment, the compound of Formula III is a compound of Formula IV:

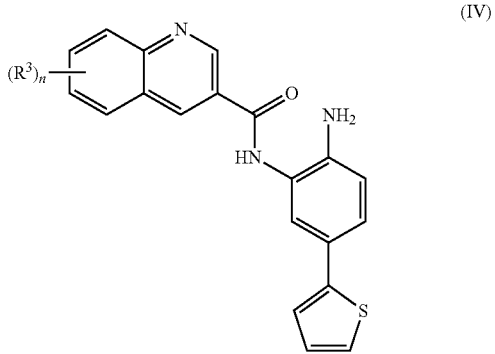

(IV)

or a pharmaceutically acceptable salt thereof.

In yet another aspect, provided herein are pharmaceutical compositions comprising any of the compounds described herein, or a pharmaceutically acceptable salt thereof, together with a pharmaceutically acceptable carrier.

In still another aspect, provided herein are methods of inhibiting the activity of HDAC1 and/or HDAC2 in a subject of need thereof, comprising administering to the subject any of the compounds or compositions described herein.

In an aspect, provided herein are methods of treating a disease mediated by HDAC1 and/or HDAC2 in a subject of need thereof, comprising administering to the subject any of the compounds or compositions described herein.

DETAILED DESCRIPTION

Provided herein are compounds, e.g., the compounds of Formulae I, II, III, and IV, or pharmaceutically acceptable salts thereof, that are useful in the treatment of cancer, myelodysplastic syndrome or hemoglobinopathy in a subject.

In a non-limiting aspect, these compounds can inhibit histone deacetylases. In a particular embodiment, the compounds provided herein are considered HDAC1 and/or HDAC2 inhibitors. As such, in one aspect, the compounds provided herein are useful in the treatment of cancer, myelodysplastic syndrome or hemoglobinopathy in a subject by acting as a HDAC1 and/or HDAC2 inhibitor.

Definitions

Listed below are definitions of various terms used herein. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or +10%, including ±5%, 1%, and ±0.1% from the specified value, as such variations are appropriate to perform the disclosed methods.

The term "treat," "treated," "treating," or "treatment" includes the diminishment or alleviation of at least one symptom associated or caused by the state, disorder or disease being treated. In certain embodiments, the treatment comprises bringing into contact with HDAC1 and/or HDAC2 an effective amount of a compound provided herein for conditions related to cancers, hemoglobinopathies, or myelodysplastic syndrome.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual," or "subject" refers to a human or a non-human mammal. Non-human mammals include, for example, livestock and pets, such as ovine, bovine, porcine, canine, feline and marine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts described herein include the conventional nontoxic salts of the parent compound formed, for example, from non-toxic inorganic or organic acids. The pharmaceutically acceptable salts discussed herein can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. The phrase "pharmaceutically acceptable salt" is not limited to a mono, or 1:1, salt. For example, "pharmaceutically acceptable salt" also includes bis-salts, such as a bis-hydrochloride salt. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound disclosed herein, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound disclosed herein, and are physiologically acceptable to the patient. Supplementary active compounds may also be incorporated into the compositions. The "pharmaceutically acceptable carrier" may further include a pharmaceutically acceptable salt of the compound disclosed herein. Other additional ingredients that may be included in the pharmaceutical compositions are known in the art and described, for example, in Remington's Pharmaceutical Sciences (Genaro, Ed., Mack Publishing Co., 1985, Easton, Pa.), which is incorporated herein by reference.

The term "HDAC" refers to histone deacetylases, which are enzymes that remove the acetyl groups from the lysine residues in core histones, thus leading to the formation of a condensed and transcriptionally silenced chromatin. There are currently 18 known histone deacetylases, which are classified into four groups. Class I HDACs, which include HDAC1, HDAC2, HDAC3, and HDAC8, are related to the yeast RPD3 gene. Class II HDACs, which include HDAC4, HDAC5, HDAC6, HDAC7, HDAC9, and HDAC10, are related to the yeast Hda1 gene. Class III HDACs, which are also known as the sirtuins are related to the Sir2 gene and include SIRT1-7. Class IV HDACs, which contains only HDAC11, has features of both Class I and II HDACs. The term "HDAC" refers to any one or more of the 18 known histone deacetylases, unless otherwise specified.

As used herein, the term "alkyl," by itself or as part of another substituent means, unless otherwise stated, a straight or branched chain hydrocarbon having the number of carbon atoms designated (i.e., $C_1$-$C_6$-alkyl means an alkyl having one to six carbon atoms) and includes straight and branched chains. In an embodiment, $C_1$-$C_6$ alkyl groups are provided herein. Examples include methyl, ethyl, propyl, isopropyl, butyl, isobutyl, tert-butyl, pentyl, neopentyl, and hexyl. Other examples of $C_1$-$C_6$-alkyl include ethyl, methyl, isopropyl, isobutyl, n-pentyl, and n-hexyl.

As used herein, the term "alkoxy," refers to the group —O-alkyl, wherein alkyl is as defined herein. Alkoxy includes, by way of example, methoxy, ethoxy, n-propoxy, isopropoxy, n-butoxy, sec-butoxy, t-butoxy and the like. In an embodiment, $C_1$-$C_6$ alkoxy groups are provided herein.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" means a non-aromatic carbocyclic system that is partially or fully saturated having 1, 2 or 3 rings wherein such rings may be fused. The term "fused" means that a second ring is present (i.e., attached or formed) by having two adjacent atoms in common (i.e., shared) with the first ring. Cycloalkyl also includes bicyclic structures that may be bridged or spirocyclic in nature with each individual ring within the bicycle varying from 3-8 atoms. The term "cycloalkyl" includes, but is not limited to, cyclopropyl, cyclobutyl, cyclopentyl, cyclohexyl, bicyclo[3.1.0]hexyl, spiro[3.3]heptanyl, and bicyclo[1.1.1]pentyl. In an embodiment, $C_4$-$C_7$ cycloalkyl groups are provided herein.

As used herein, the term "heterocycloalkyl" means a non-aromatic carbocyclic system containing 1, 2, 3 or 4 heteroatoms selected independently from N, O, and S and having 1, 2 or 3 rings wherein such rings may be fused, wherein fused is defined above. Heterocycloalkyl also includes bicyclic structures that may be bridged or spirocyclic in nature with each individual ring within the bicycle varying from 3-8 atoms, and containing 0, 1, or 2 N, O, or S atoms. The term "heterocycloalkyl" includes cyclic esters (i.e., lactones) and cyclic amides (i.e., lactams) and also specifically includes, but is not limited to, epoxidyl, oxetanyl, tetrahydrofuranyl, tetrahydropyranyl (i.e., oxanyl), pyranyl, dioxanyl, aziridinyl, azetidinyl, pyrrolidinyl, 2,5-dihydro-1H-pyrrolyl, oxazolidinyl, thiazolidinyl, piperidinyl, morpholinyl, piperazinyl, thiomorpholinyl, 1,3-oxazinanyl, 1,3-thiazinanyl, 2-azabicyclo[2.1.1]hexanyl, 5-azabicyclo[2.1.1]hexanyl, 6-azabicyclo[3.1.1] heptanyl, 2-azabicyclo[2.2.1]heptanyl, 3-azabicyclo[3.1.1]heptanyl, 2-azabicyclo[3.1.1]heptanyl, 3-azabicyclo[3.1.0]hexanyl, 2-azabicyclo[3.1.0]hexanyl, 3-azabicyclo[3.2.1]octanyl, 8-azabicyclo[3.2.1]octanyl, 3-oxa-7-azabicyclo[3.3.1]nonanyl, 3-oxa-9-azabicyclo[3.3.1]nonanyl, 2-oxa-5-azabicyclo[2.2.1]heptanyl, 6-oxa-3-azabicyclo[3.1.1]heptanyl, 2-azaspiro[3.3]heptanyl, 2-oxa-6-azaspiro[3.3]heptanyl, 2-oxaspiro[3.3]heptanyl, 2-oxaspiro[3.5]nonanyl, 3-oxaspiro[5.3]nonanyl, and 8-oxabicyclo[3.2.1]octanyl. In an embodiment, $C_2$-$C_7$ heterocycloalkyl groups are provided herein.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl" means an aromatic carbocyclic system containing 1, 2 or 3 rings, wherein such rings may be fused, wherein fused is defined above. If the rings are fused, one of the rings must be fully unsaturated and the fused ring(s) may be fully saturated, partially unsaturated or fully unsaturated. The term "aryl" includes, but is not limited to, phenyl, naphthyl, indanyl, and 1,2,3,4-tetrahydronaphthalenyl. In some embodiments, aryl groups have 6 carbon atoms. In some embodiments, aryl groups have from six to ten carbon atoms. In some embodiments, aryl groups have from six to sixteen carbon atoms. In an embodiment, $C_5$-$C_7$ aryl groups are provided herein.

As used herein, the term "heteroaryl" means an aromatic carbocyclic system containing 1, 2, 3, or 4 heteroatoms selected independently from N, O, and S and having 1, 2, or 3 rings wherein such rings may be fused, wherein fused is defined above. The term "heteroaryl" includes, but is not limited to, furanyl, thiophenyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, imidazo[1,2-a]pyridinyl, pyrazolo[1,5-a]pyridinyl, 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydrocyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazolyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl. In an embodiment, $C_2$-$C_7$ heteroaryl groups are provided herein.

It is to be understood that if an aryl, heteroaryl, cycloalkyl, or heterocycloalkyl moiety may be bonded or otherwise attached to a designated moiety through differing ring atoms (i.e., shown or described without denotation of a specific point of attachment), then all possible points are intended, whether through a carbon atom or, for example, a trivalent nitrogen atom. For example, the term "pyridinyl" means 2-, 3- or 4-pyridinyl, the term "thienyl" means 2- or 3-thioenyl, and so forth.

As used herein, the term "substituted" means that an atom or group of atoms has replaced hydrogen as the substituent attached to another group.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

Compounds

In an aspect, provided herein are compounds of Formula I:

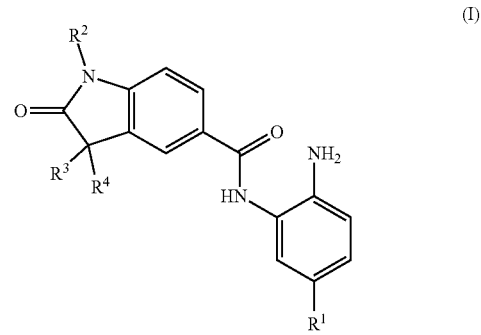

or a pharmaceutically acceptable salt thereof;
wherein:

$R^1$ is selected from the group consisting of aryl or heteroaryl, wherein aryl or heteroaryl are optionally substituted with —OH or —OSO$_2$NHCH$_3$;

$R^2$ is selected from the group consisting of —H, $C_1$-$C_6$ alkyl, alkyl-cycloalkyl, alkyl-heterocycloalkyl, alkyl-aryl, alkyl-heteroaryl, aryl, heteroaryl, and halo; and $R^3$ and $R^4$ are independently, at each occurrence, selected from the group consisting of —H, halo, alkyl, aryl, heteroaryl, cycloalkyl, and heterocycloalkyl.

In an embodiment, $R^1$ is selected from the group consisting of aryl, aryl-OH, and heteroaryl; $R^2$ is selected from the group consisting of —H, methyl, alkyl-cycloalkyl, and alkyl-heterocycloalkyl; and $R^3$ and $R^4$ are independently, at each occurrence, selected from the group consisting of —H, halo, and methyl.

In another embodiment, $R^1$ is selected from the group consisting of phenyl, phenyl-OH, thienyl, and furanyl. In yet another embodiment, $R^1$ is phenyl. In still another embodiment, $R^1$ is phenyl-OH. In an embodiment, $R^1$ is thienyl. In another embodiment, $R^1$ is furanyl.

In yet another embodiment, $R^2$ is selected from the group consisting of —H, methyl, CH$_2$-cycloalkyl, and $C_1$-$C_3$ alkyl-5-6 membered heterocycloalkyl. In another embodiment, $R^2$ is —H. In yet another embodiment, $R^2$ is methyl. In still another embodiment, $R^2$ is CH$_2$-cycloalkyl. In an embodiment, $R^2$ is $C_1$-$C_3$ alkyl-5-6 membered heterocycloalkyl.

In another embodiment, $R^3$ and $R^4$ are independently, at each occurrence, selected from the group consisting of —H, halo, and methyl. In yet another embodiment, $R^3$ and $R^4$ are independently, at each occurrence, —H. In still another embodiment, $R^3$ and $R^4$ are independently, at each occurrence, halo. In an embodiment, $R^3$ and $R^4$ are independently, at each occurrence, methyl.

In another embodiment, aryl is a 6-10 membered aromatic ring and heteroaryl is a 5-10 membered heteroaromatic ring.

In another aspect, provided herein are compounds of Formula II:

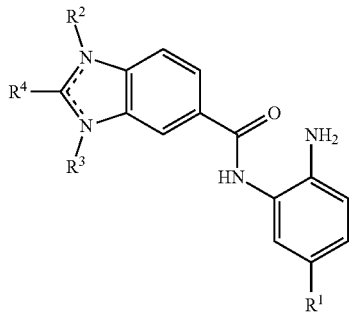

or a pharmaceutically acceptable salt thereof;
wherein:

$R^1$ is selected from the group consisting of aryl and heteroaryl, wherein aryl or heteroaryl are optionally substituted with —OH or —OSO$_2$NHCH$_3$;

$R^2$ is selected from the group consisting of absent, —H, $C_1$-$C_6$ alkyl, alkyl-cycloalkyl, alkyl-heterocycloalkyl, aryl, and heteroaryl;

$R^3$ is selected from the group consisting of absent, —H, $C_1$-$C_6$ alkyl, alkyl-cycloalkyl, alkyl-heterocycloalkyl, aryl, and heteroaryl;

$R^4$ is selected from the group consisting of —H, —OH, alkyl, aryl, cycloalkyl, and heteroaryl; and ═════ indicates an optional double bond.

In an embodiment of Formula II, $R^1$ is aryl or heteroaryl; $R^2$ is selected from the group consisting of absent, —H, methyl, and alkyl-heterocycloalkyl; $R^3$ is selected from the group consisting of absent, —H, and alkyl-heterocycloalkyl; and $R^4$ is selected from the group consisting of —H, —OH, cycloalkyl, and methyl.

In another embodiment, $R^1$ is phenyl or thienyl. In yet another embodiment, $R^1$ is phenyl. In still another embodiment, $R^1$ is thienyl.

In an embodiment, $R^2$ is selected from the group consisting of absent, —H, methyl, and $C_2$-alkyl-5-6 membered heterocycloalkyl. In still another embodiment, $R^2$ is absent. In an embodiment, $R^2$ is —H. In another embodiment, $R^2$ is methyl. In yet another embodiment, $R^2$ is $C_2$-alkyl-5-6 membered heterocycloalkyl.

In still another embodiment, $R^3$ is selected from the group consisting of absent, —H, and —$C_2$-alkyl-5-6 membered heterocycloalkyl. In an embodiment, $R^3$ is absent. In another embodiment, $R^3$ is —H. In yet another embodiment, $R^3$ is —$C_2$-alkyl-5-6 membered heterocycloalkyl.

In still another embodiment, $R^4$ is selected from the group consisting of —H, cyclopropyl, and methyl. In an embodiment, $R^4$ is —H. In another embodiment $R^4$ is cyclopropyl. In yet another embodiment, $R^4$ is methyl.

In another embodiment, aryl is a 6-10 membered aromatic ring and heteroaryl is a 5-10 membered heteroaromatic ring.

In still another embodiment, the compound of Formula I or Formula II is selected from the group consisting of:

TABLE 1

| Compound No. | Structure |
|---|---|
| 001 | 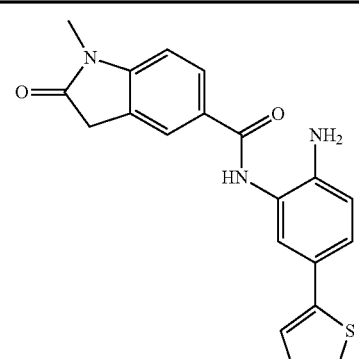 |
| 002 | 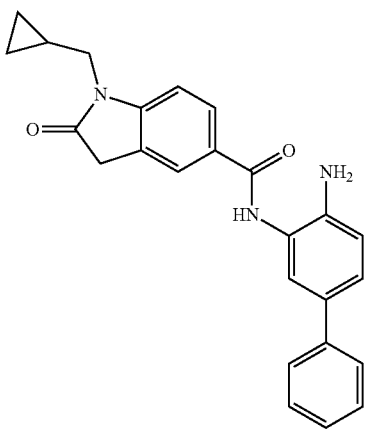 [SMILES: Nc1ccc(-c2ccccc2)cc1NC(=O)c1ccc2c(c1)CC(=O)N2CC1CC1] |
| 003 | 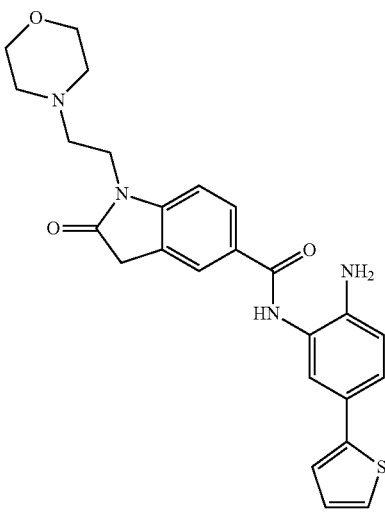 [SMILES: Nc1ccc(-c2cccs2)cc1NC(=O)c1ccc2c(c1)CC(=O)N2CCN1CCOCC1] |

TABLE 1-continued
| Compound No. | Structure |
|---|---|
| 004 |  |
| 005 |  |
| 006 | 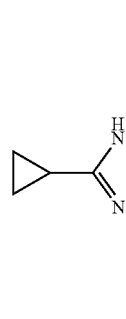 |
| 007 | 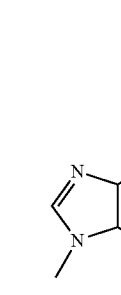 |
| 008 | 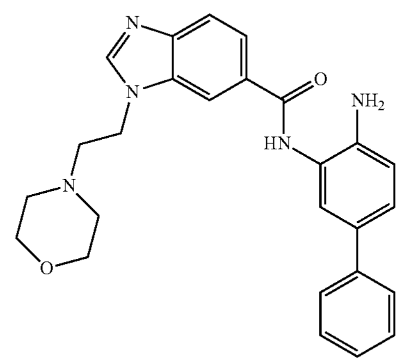 [SMILES: Nc1ccc(-c2ccccc2)cc1NC(=O)c1ccc2ncn(CCN3CCOCC3)c2c1] |
| 009 | 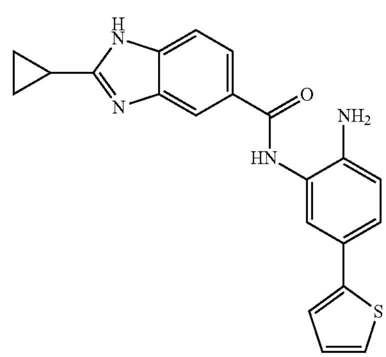 [SMILES: Nc1ccc(-c2cccs2)cc1NC(=O)c1ccc2[nH]c(C3CC3)nc2c1] |
| 010 | 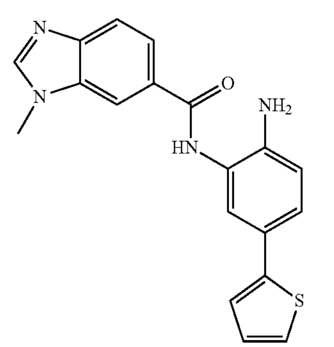 [SMILES: Cn1cnc2ccc(C(=O)Nc3cc(-c4cccs4)ccc3N)cc21] |

TABLE 1-continued
| Compound No. | Structure |
|---|---|
| 011 | 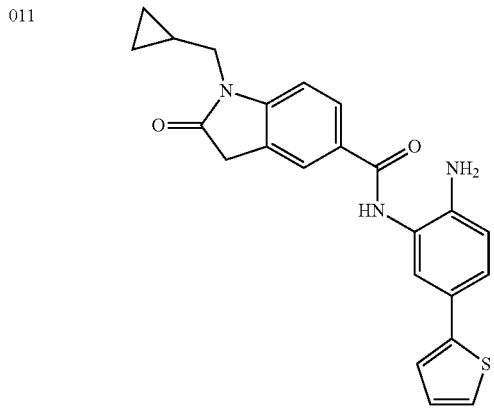 |
| 012 | 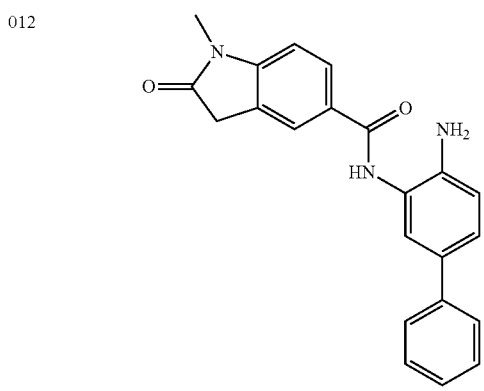 |
| 013 | 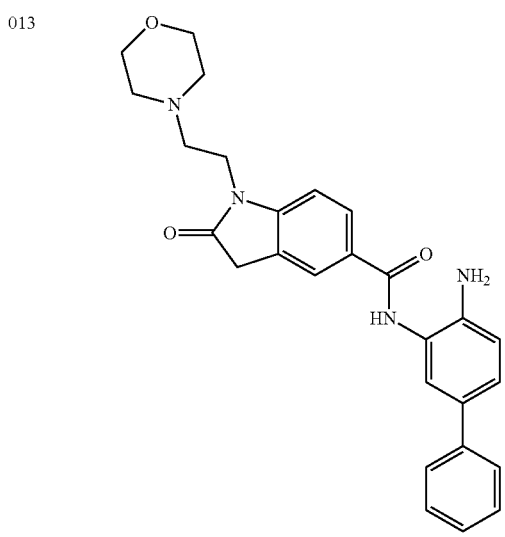 |
TABLE 1-continued
| Compound No. | Structure |
|---|---|
| 014 | 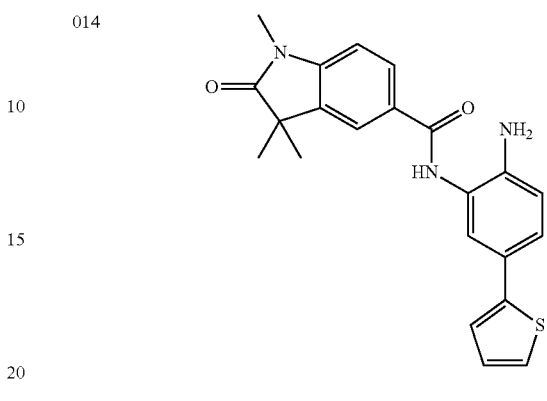 |
| 015 | 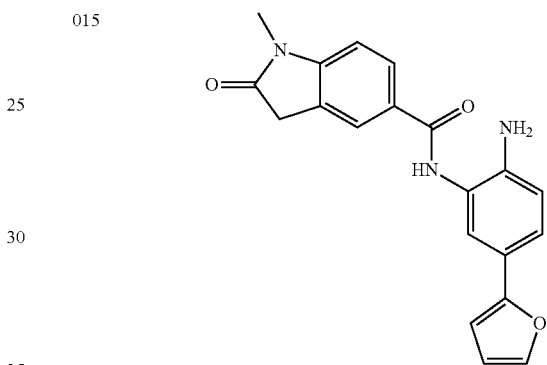 |
| 016 | 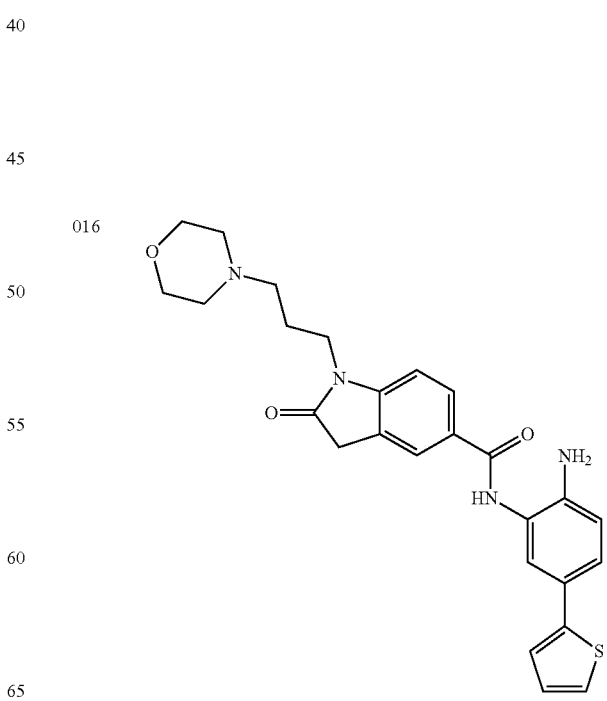 |

TABLE 1-continued
| Compound No. | Structure |
|---|---|
| 017 | 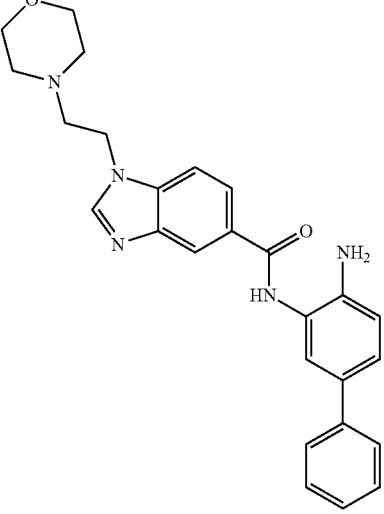 |
| 018 | 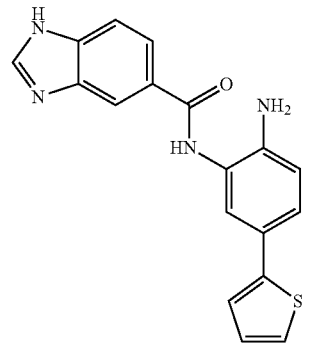 [SMILES: Nc1ccc(-c2cccs2)cc1NC(=O)c1ccc2[nH]cnc2c1] |
| 019 | 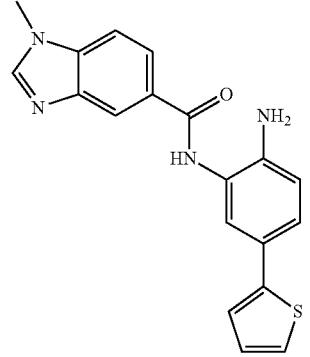 [SMILES: Cn1cnc2cc(C(=O)Nc3cc(-c4cccs4)ccc3N)ccc21] |
| 020 | 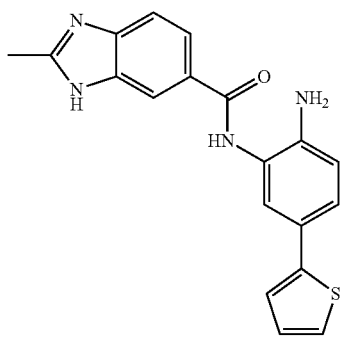 [SMILES: Cc1nc2ccc(C(=O)Nc3cc(-c4cccs4)ccc3N)cc2[nH]1] |
| 021 | 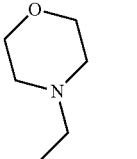 |
| 022 | 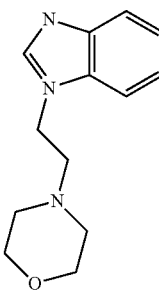 |
| 023 | 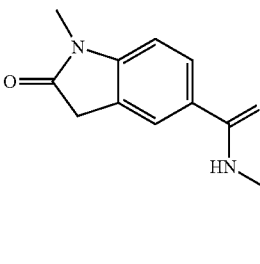 |
or a pharmaceutically acceptable salt thereof.

In yet another aspect, provided herein is a compound of Formula III:

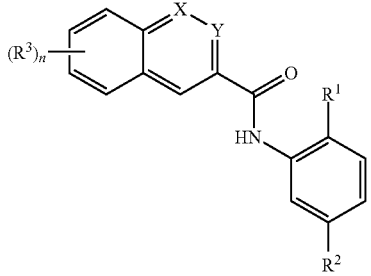

(III)

or a pharmaceutically acceptable salt thereof;
wherein:
X and Y are, independently at each occurrence, selected from the group consisting of CH and N, provided at least one of X and Y are N;
$R^1$ is —N($R^4$)$_2$ or —O$R^4$;
$R^2$ is selected from the group consisting of halo, aryl, and heteroaryl; wherein aryl or heteroaryl are optionally substituted by one or more $R^5$ groups;
$R^3$ is independently, at each occurrence, selected from the group consisting of halo, cycloalkyl, heterocycloalkyl, —N($R^6$)—$C_1$-$C_3$ alkyl-N($R^6$)$_2$, —O—$C_1$-$C_3$ alkyl-N($R^6$)$_2$, and —N($R^6$)—$C_1$-$C_3$ alkyl-O$R^6$; wherein cycloalkyl and heterocycloalkyl are optionally substituted by one or more $R^5$ groups;
$R^4$ is independently, at each occurrence, selected from the group consisting of —H, $C_1$-$C_6$ alkyl, and $C_1$-$C_6$ alkoxy;
$R^5$ is independently, at each occurrence, —H or $C_1$-$C_6$ alkyl;
$R^6$ is independently, at each occurrence, selected from the group consisting of —H, $C_1$-$C_6$ alkyl, and $C_1$-$C_6$ alkoxy; and
n is 0, 1, 2, or 3.

In an embodiment of Formula III, $R^1$ is —NH$_2$ or —OH; $R^2$ is halo or heteroaryl, wherein heteroaryl is optionally substituted by one or more $R^5$; $R^3$ is independently, at each occurrence, selected from the group consisting of cycloalkyl, heterocycloalkyl, —N($R^6$)—$C_1$-$C_3$ alkyl-N($R^6$)$_2$, —O—$C_1$-$C_3$ alkyl-N($R^6$)$_2$, and —N($R^6$)—$C_1$-$C_3$ alkyl-O$R^6$; wherein cycloalkyl and heterocycloalkyl are optionally substituted by one or more $R^5$; $R^4$ is independently, at each occurrence, —H or $C_1$-$C_6$ alkyl; $R^5$ is independently, at each occurrence, —H or $C_1$-$C_6$ alkyl; $R^6$ is independently, at each occurrence, —H or $C_1$-$C_6$ alkyl; and n is 1, 2, or 3.

In another embodiment, $R^1$ is —NH$_2$ or —OH. In yet another embodiment, $R^1$ is —NH$_2$. In still another embodiment, $R^1$ is —OH.

In another embodiment, $R^2$ is halo or heteroaryl, wherein heteroaryl is optionally substituted by one or more R$_5$. In an embodiment, $R^2$ is halo. In another embodiment, $R^2$ is heteroaryl, wherein heteroaryl is optionally substituted by one or more $R^5$.

In yet another embodiment, $R^3$ is independently, at each occurrence, selected from the group consisting of halo, cycloalkyl, heterocycloalkyl, —N($R^6$)—$C_1$-$C_3$ alkyl-N($R^6$)$_2$, —O—$C_1$-$C_3$ alkyl-N($R^6$)$_2$, and —N($R^6$)—$C_1$-$C_3$ alkyl-O$R^6$, wherein cycloalkyl and heterocycloalkyl are optionally substituted by one or more $R^5$ groups. In still another embodiment, n is 1 and $R^3$ is cycloalkyl, wherein cycloalkyl is optionally substituted by one or more $R^5$. In an embodiment, n is 1 and $R^3$ is heterocycloalkyl, wherein heterocycloalkyl is optionally substituted by one or more $R^5$. In another embodiment, n is 1, and $R^3$ is —N($R^6$)—$C_1$-$C_3$ alkyl-N($R^6$)$_2$. In yet another embodiment, n is 1, and $R^3$ is —O—$C_1$-$C_3$ alkyl-N($R^6$)$_2$. In still another embodiment, n is 1, and $R^3$ is —N($R^6$)—$C_1$-$C_3$ alkyl-O$R^6$.

In an embodiment, $R^4$ is independently, at each occurrence, —H or $C_1$-$C_6$ alkyl. In another embodiment, $R^4$ is —H. In yet another embodiment, $R^4$ is $C_1$-$C_6$ alkyl.

In still another embodiment, $R^5$ is independently, at each occurrence, —H or $C_1$-$C_6$ alkyl. In an embodiment, $R^5$ is —H. In another embodiment, $R^5$ is $C_1$-$C_6$ alkyl.

In yet another embodiment, $R^6$ is independently, at each occurrence, —H or $C_1$-$C_6$ alkyl. In still another embodiment, $R^6$ is —H. In an embodiment, $R^6$ is $C_1$-$C_6$ alkyl.

In another embodiment, n is 1 or 2. In yet another embodiment, n is 1. In still another embodiment, n is 2. In an embodiment, n is 3.

In another embodiment, the compound of Formula III is a compound of Formula IV:

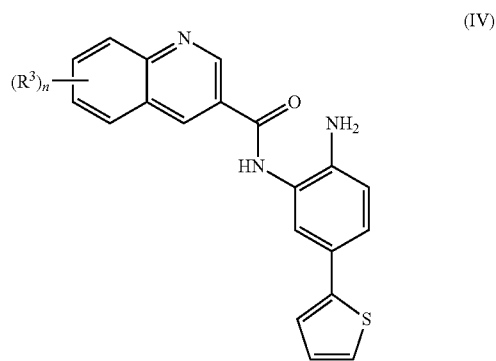

(IV)

or a pharmaceutically acceptable salt thereof.

In an embodiment of Formula IV, $R^3$ is independently, at each occurrence, selected from the group consisting of cycloalkyl, heterocycloalkyl, —N($R^6$)—$C_1$-$C_3$ alkyl-N($R^6$)$_2$, —O—$C_1$-$C_3$ alkyl-N($R^6$)$_2$, and —N($R^6$)—$C_1$-$C_3$ alkyl-O$R^6$, wherein cycloalkyl and heterocycloalkyl are optionally substituted by one or more $R^5$. In yet another embodiment, n is 1, and $R^3$ is cycloalkyl optionally substituted by one or more $R^5$. In still another embodiment, n is 1, and $R^3$ is heterocycloalkyl optionally substituted by one or more $R^5$. In an embodiment, n is 1, and $R^3$ is —N($R^6$)—$C_1$-$C_3$ alkyl-N($R^6$)$_2$. In another embodiment, n is 1, and $R^3$ is —O—$C_1$-$C_3$ alkyl-N($R^6$)$_2$. In yet another embodiment, n is 1, and $R^3$ is —N($R^6$)—$C_1$-$C_3$ alkyl-O$R^6$.

In another embodiment of Formula IV, $R^6$ is, independently at each occurrence, —H or $C_1$-$C_6$ alkyl. In yet another embodiment, $R^6$ is —H. In still another embodiment, $R^6$ is $C_1$-$C_6$ alkyl.

In an embodiment, n is 1, 2, or 3. In another embodiment, n is 1. In yet another embodiment, n is 2. In still another embodiment, n is 3.

In an embodiment, the compound of Formula III or Formula IV is selected from the group consisting of:
TABLE 2
| Compound No. | Structure |
|---|---|
| 024 | 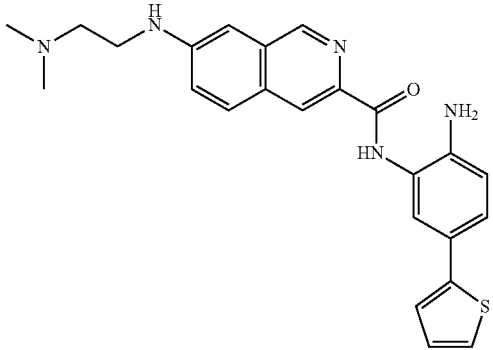 [SMILES: CN(C)CCNc1ccc2cc(C(=O)Nc3cc(-c4cccs4)ccc3N)ncc2c1] |
| 025 | 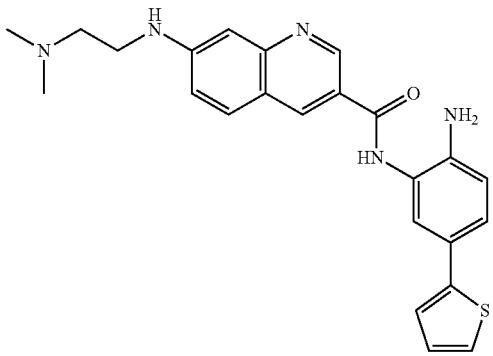 [SMILES: CN(C)CCNc1ccc2cc(C(=O)Nc3cc(-c4cccs4)ccc3N)cnc2c1] |
| 026 | 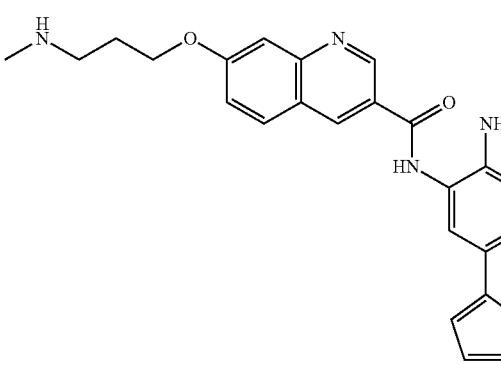 |
| 027 | 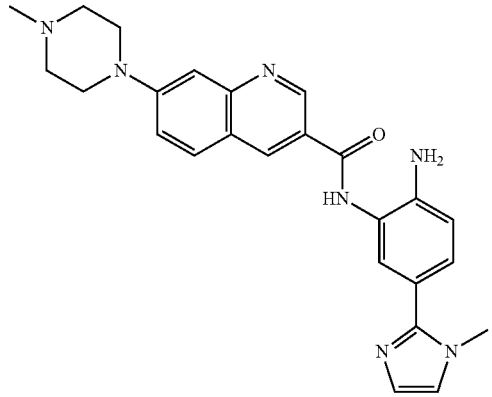 |
TABLE 2-continued
| Compound No. | Structure |
|---|---|
| 028 | 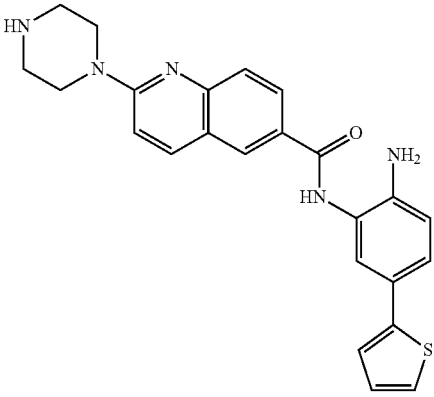 [SMILES: Nc1ccc(-c2cccs2)cc1NC(=O)c1ccc2nc(N3CCNCC3)ccc2c1] |
| 029 | 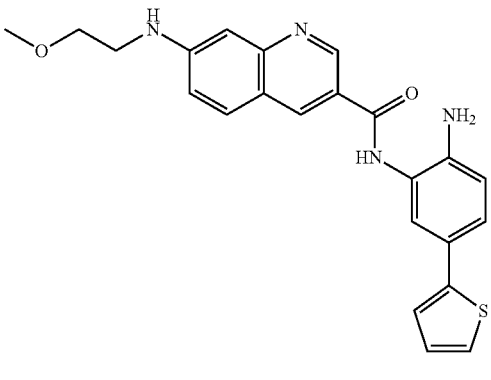 [SMILES: COCCNc1ccc2cc(C(=O)Nc3cc(-c4cccs4)ccc3N)cnc2c1] |
| 030 | 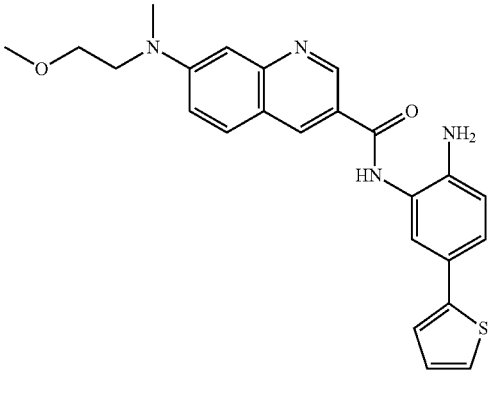 [SMILES: COCCN(C)c1ccc2cc(C(=O)Nc3cc(-c4cccs4)ccc3N)cnc2c1] |
| 031 | 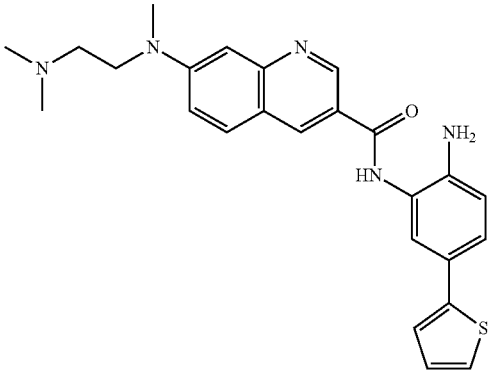 [SMILES: CN(C)CCN(C)c1ccc2cc(C(=O)Nc3cc(-c4cccs4)ccc3N)cnc2c1] |

TABLE 2-continued

| Compound No. | Structure |
|---|---|
| 032 | (structure shown) | or a pharmaceutically acceptable salt thereof.

In an aspect, provided herein are pharmaceutical compositions comprising any of the compounds described herein, or a pharmaceutically acceptable salt thereof, together with a pharmaceutically acceptable carrier.

In one embodiment, the disclosed compounds may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2$H, $^3$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In another embodiment, isotopically-labeled compounds are useful in drug or substrate tissue distribution studies. In another embodiment, substitution with heavier isotopes such as deuterium affords greater metabolic stability (for example, increased in vivo half-life or reduced dosage requirements). In yet another embodiment, the compounds described herein include a $^2$H (i.e., deuterium) isotope.

In still another embodiment, substitution with positron emitting isotopes, such as $^{11}$C, $^{18}$F, $^{15}$O and $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

The specific compounds described herein, and other compounds encompassed by one or more of the formulas described herein having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compounds as described herein are modified by the use of appropriate reagents and conditions, for the introduction of the various moieties found in the Formulas as provided herein.

Compounds described herein are synthesized using any suitable procedures starting from compounds that are available from commercial sources, or are prepared using procedures described herein.

Methods of Treatment

The compounds provided herein can be used in a method of treating a disease or condition in a subject, said method comprising administering to the subject in need thereof a compound provided herein, or pharmaceutically acceptable salt thereof, or a pharmaceutical composition comprising a compound provided herein, or pharmaceutically acceptable salt thereof.

In an aspect, provided herein is a method of selectively inhibiting HDAC1 and/or HDAC2 over other HDACs (e.g., HDAC3 and HDAC6) in a subject in need thereof, comprising administering to the subject a compound of Formula I, II, III, IV, or any of the compounds of Table 1 or Table 2, or pharmaceutically acceptable salts thereof.

In an embodiment, a compound provided herein has a selectivity for HDAC1 and/or HDAC2 of 5 to 1000 fold over other HDACs.

In another embodiment, a compound provided herein has a selectivity for HDAC1 and/or HDAC2 when tested in a HDAC enzyme assay of about 5 to 1000 fold over other HDACs.

In certain embodiments, the compound has a selectivity for HDAC1 and/or HDAC2 of 15 to 40 fold over other HDACs.

In another aspect, provided herein is a method of treating a disease mediated by HDAC1 and/or HDAC2 in a subject in need thereof, comprising administering to the subject a compound of Formula I, II, III, IV, or any of the compounds of Table 1 or Table 2.

In an embodiment, the disease is selected from the group consisting of alopecia, spinal muscular atrophy, inflammatory bowel disease, and Crohn's ulcerative colitis.

In an embodiment, the compounds provided herein are able to treat a subject suffering from or susceptible to a hemoglobinopathy. In another embodiment, the compounds are able to treat sickle-cell disease or beta-thalassemia.

In another embodiment, the compounds provided herein are useful in the treatment of myelodysplastic syndromes.

In an aspect, provided herein is a method of treating cancer in a subject in need thereof, comprising administering to the subject a therapeutically effective amount of a compound provided herein, or pharmaceutically acceptable salt thereof.

In still another embodiment, the cancer is lung cancer, colon and rectal cancer, breast cancer, prostate cancer, liver cancer, pancreatic cancer, brain cancer, kidney cancer, ovarian cancer, stomach cancer, skin cancer, bone cancer, gastric cancer, breast cancer, glioma, glioblastoma, neuroblastoma, hepatocellular carcinoma, papillary renal carcinoma, head and neck squamous cell carcinoma, leukemia, lymphomas, myelomas, retinoblastoma, cervical cancer, melanoma and/or skin cancer, bladder cancer, uterine cancer, testicular cancer, esophageal cancer, and solid tumors. In some embodiments, the cancer is lung cancer, colon cancer, breast cancer, neuroblastoma, leukemia, or lymphomas. In other embodiments, the cancer is lung cancer, colon cancer, breast cancer, neuroblastoma, leukemia, or lymphoma. In a further embodiment, the cancer is non-small cell lung cancer (NSCLC) or small cell lung cancer.

In an embodiment, the cancer is neuroblastoma.

In another embodiment, the cancer is a hematologic cancer. In yet another embodiment, the hematologic cancer is leukemia or lymphoma. In still another embodiment, the lymphoma is Hodgkin's lymphoma or Non-Hodgkin's lymphoma. In an embodiment, the leukemia is myeloid, lymphocytic, myelocytic, lymphoblastic, or megakaryotic leukemia. In another embodiment, the leukemia is acute myelogenous leukemia or megakaryocytic leukemia.

In another aspect, provided herein is a method of treating or preventing hearing loss in a subject in need thereof comprising administering to a subject a therapeutically effective amount of a compound disclosed herein, or a pharmaceutically acceptable salt thereof.

In another aspect, provided herein is a method of treating sickle cell disease, beta thalassemia, myelodysplastic syndrome, acute myelogenous leukemia, neuroblastoma, or megakaryocytic leukemia in a subject in need thereof, comprising administering to the subject a therapeutically effective amount of a provided herein, or a pharmaceutically acceptable salt thereof.

In yet another aspect, provided herein is a method for the treatment of a disease mediated by HDAC1 and/or HDAC2 in a subject in need thereof, comprising administering to the subject a therapeutically effective amount of a compound as described herein. In an embodiment, the subject is identified as in need of such treatment. In another embodiment, the method of treatment comprises administering to the subject a therapeutically effective amount of a compound provided herein, or a pharmaceutical composition comprising a compound provided herein, in such amounts and for such time as is necessary to achieve the desired result.

In yet another embodiment, the method involves the administration of a therapeutically effective amount of a compound provided herein, or a pharmaceutically acceptable salt thereof, to a subject (including, but not limited to a human or animal) in need of treatment (including a subject identified as in need).

Administration/Dosage/Formulations

In another aspect, provided herein is a pharmaceutical composition comprising at least one compound disclosed herein, together with a pharmaceutically acceptable carrier.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could begin administration of the pharmaceutical composition to dose the disclosed compound at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of the disclosed compound calculated to produce the desired therapeutic effect in association with the required pharmaceutical vehicle. The dosage unit forms are dictated by and directly dependent on (a) the unique characteristics of the disclosed compound and the particular therapeutic effect to be achieved, and (b) the limitations inherent in the art of compounding/formulating such a disclosed compound for the treatment of pain, a depressive disorder, or drug addiction in a patient.

In one embodiment, the compounds provided herein are formulated using one or more pharmaceutically acceptable excipients or carriers. In one embodiment, the pharmaceutical compositions provided herein comprise a therapeutically effective amount of a disclosed compound and a pharmaceutically acceptable carrier.

Routes of administration of any of the compositions discussed herein include oral, nasal, rectal, intravaginal, parenteral, buccal, sublingual or topical. The compounds may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration. In one embodiment, the preferred route of administration is oral.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions are not limited to the particular formulations and compositions that are described herein.

For oral application, particularly suitable are tablets, dragees, liquids, drops, suppositories, or capsules, caplets and gel caps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the disclosed compounds may be formulated for injection or infusion, for example, intravenous, intramuscular or subcutaneous injection or infusion, or for administration in a bolus dose or continuous infusion. Suspensions, solutions or emulsions in an oily or aqueous vehicle, optionally containing other formulatory agents such as suspending, stabilizing or dispersing agents may be used.

Those skilled in the art will recognize, or be able to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

The following examples further illustrate aspects of the present disclosure. However, they are in no way a limitation of the teachings of the present disclosure as set forth.

EXAMPLES

The compounds and methods disclosed herein are further illustrated by the following examples, which should not be construed as further limiting. The practice of the present disclosure will employ, unless otherwise indicated, conventional techniques of organic synthesis, cell biology, cell culture, and molecular biology, which are within the skill of the art.

Abbreviations

Ac acetyl
° C. degree Celsius
dba dibenzylideneacetone
DCM dichloromethane
DIPEA N,N-Diisopropylethylamine
DMAP 4-dimethylaminopyridine
DMF dimethylformamide
DMSO dimethylsulfoxide
dppf 1,1'-bis(diphenylphosphino)ferrocene
EDCI 1-ethyl-3-[3-(dimethylamino)propyl]carbodiimid-hydrochloride
EA ethyl acetate
HATU O-(7-Azabenzotriazol-1-yl)-N,N,N',N'-tetramethyluronium Hexafluorophosphate
HOAt 1-hydroxy-7-azabenzotriazole
HOBt 1-hydroxybenzotriazole
HPLC high performance liquid chromatography
m-CPBA m-chloroperoxybenzoicacid
PE petroleum ether
Ph phenyl
Py pyridine
Ruphos 2-Dicyclohexylphosphino-2',6'-di-i-propoxy-1,1'-biphenyl
S-Phos 2-Dicyclohexylphosphino-2',6'-dimethoxybiphenyl
TFA trifluoroacetic acid
THE tetrahydrofuran
TLC thin layer chromatography
Tol toluene or tolyl
Xantphos 4,5-Bis(diphenylphosphino)-9,9-dimethylxanthene Synthesis Procedures Example 1—Synthesis of Compound 001

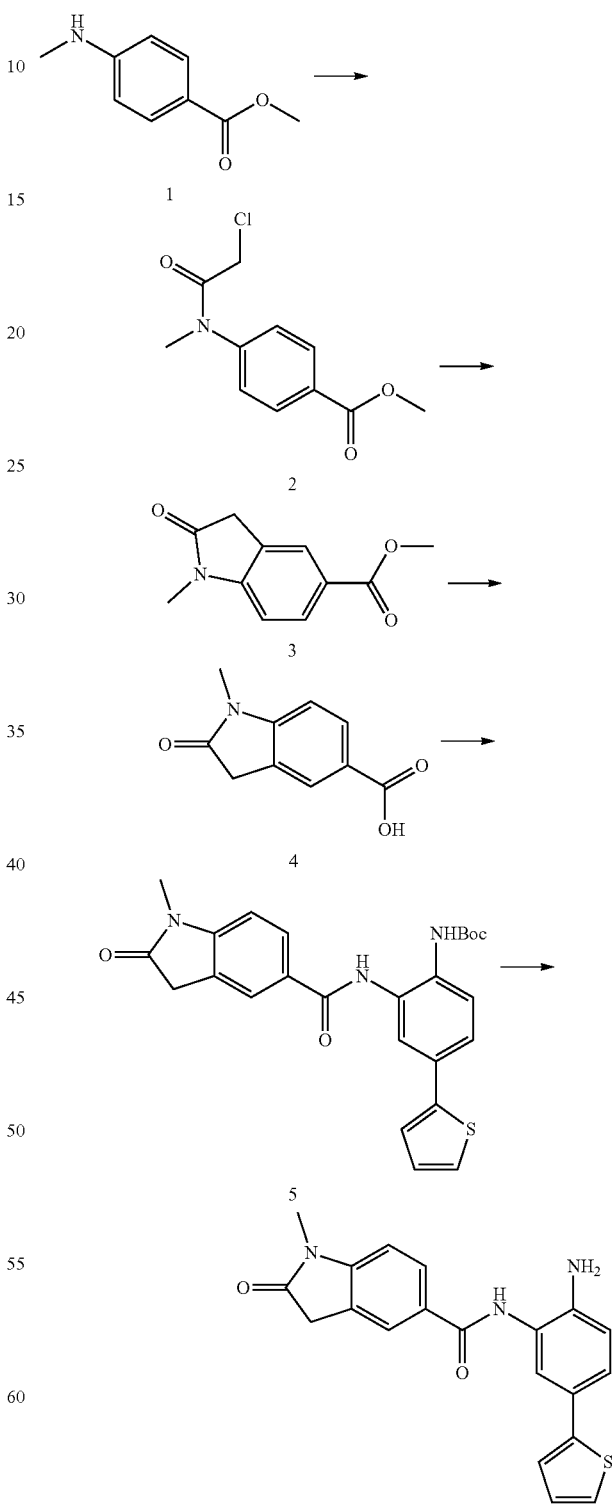

Step 1:

Methyl-4-(methylamino)benzoate (1.0 g, 6.6 mmol) and K₂CO₃ (2.28 g, 16.53 mmol) were combined in EA and water (v:v=1, 30 mL) and stirred at rt for 20 mins. 2-Chloroacetyl chloride (0.63 mL, 7.94 mmol) was added dropwise. The mixture was stirred at rt for 24 h. The organic layer was collected and dried over Na₂SO₄. The crude solution was concentrated to afford compound 2 as a white solid (0.9 g, 57%).

Step 2:

Compound 2 (0.9 g, 3.734 mmol) was dissolved in toluene (10 mL). KOAc (736 mg, 0.75 mmol), xantphos (433 mg, 0.2 eq), and Pd(OAc)₂ (168 mg, 0.2 eq) were added. The mixture was stirred at 60° C. overnight. After the reaction was complete, the mixture was filtered. The filtrate was concentrated and washed with 10 mL EA. The solid was collected to afford compound 3 (1.0 g, crude).

Step 3:

Compound 3 (1.0 g, 5 mmol) was stirred in 2M HCl (15 mL) at 100° C. overnight. The mixture was concentrated to get compound 4 (823 mg, 86%) as yellow solid.

Step 4:

To a solution of compound 4 (95 mg, 0.5 mmol) in Py (5 mL) was added EDCI (191 mg, 1 mmol) followed by amine tert-butyl 2-amino-4-(thiophen-2-yl)phenylcarbamate (123 mg, 0.9 eq). The mixture was stirred at rt overnight. The mixture was concentrated to get a residue, which was extracted with EA/water to get compound 5 (250 mg, crude).

Step 5:

Compound 5 (220 mg, crude) was dissolved in DCM (2 mL). TFA (1 mL) was added, and the reaction mixture was stirred at rt for 1 h. The mixture was concentrated to get compound 001 (38 mg, 20%) as yellow solid. LCMS: m/z=364 (M+H)⁺ ¹H NMR (400 MHz, DMSO) δ 9.65 (s, 1H), 7.97 (d, J=8.2 Hz, 1H), 7.93 (s, 1H), 7.61 (d, J=1.1 Hz, 1H), 7.52 (d, J=1.8 Hz, 1H), 7.33 (dd, J=8.4, 1.9 Hz, 1H), 7.11 (d, J=8.2 Hz, 1H), 6.82 (d, J=8.4 Hz, 1H), 6.61 (d, J=3.2 Hz, 1H), 6.51 (dd, J=3.2, 1.8 Hz, 1H), 5.14 (s, 2H), 3.64 (d, J=8.1 Hz, 2H), 3.17 (d, J=10.2 Hz, 3H).

Example 2—Synthesis of Compound 002

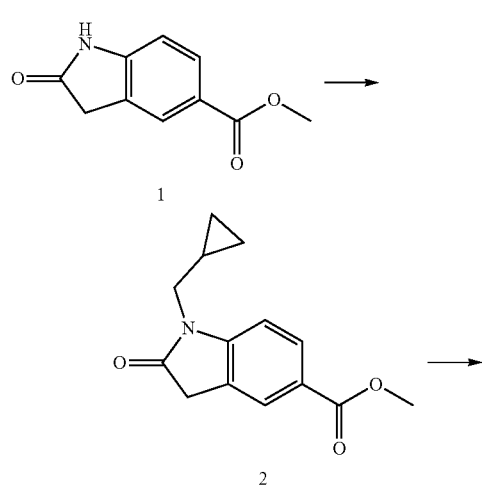

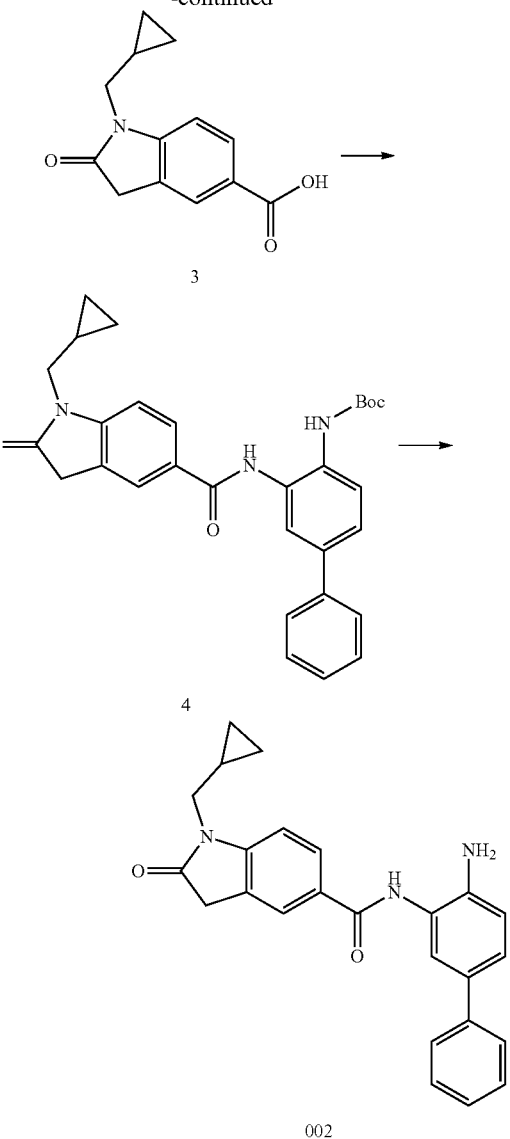

Step 1:

Methyl 2-oxoindoline-5-carboxylate (382 g, 2 mmol), (bromomethyl)cyclopropane (270 mg, 2 mmol), and K₂CO₃ (276 mg, 2 mmol) was stirred in DMF (5 mL) at rt overnight. The mixture was diluted with EA (300 mL), filtered (flash silica gel), and concentrated to get a residue, which was purified by silica gel to get Compound 2 (294 mg, 60%) as yellow solid.

Step 2:

Compound 2 (490 mg, 2 mmol) was added to 6M HCl (5 mL) and stirred at 80° C. overnight. The mixture was concentrated to get Compound 3 (462 mg, 100%) as yellow solid.

Step 3:

Compound 3 (231 mg, 1 mmol), amine tert-butyl 3-aminobiphenyl-4-ylcarbamate (284 mg, 1 mmol), and EDCI (382 mg, 2 mmol) were combined in Py (5 mL) and was stirred at rt overnight. The mixture was concentrated to get a residue, which was purified by silica gel to get Compound 4 (298 mg, 60%) as yellow solid.

Step 4:

Compound 4 (249 mg, 0.5 mmol) was dissolved in DCM (2 mL). TFA (1 mL) was added and the reaction mixture was stirred at rt for 1 h. The mixture was concentrated to get Compound 002 (119, 80%) as yellow solid. LCMS: m/z=498 (M+H)$^+$. $^1$H NMR (400 MHz, DMSO) δ 9.66 (s, 1H), 8.00 (m, 1H), 7.93 (s, 1H), 7.46 (s, 1H), 7.40 (m, 1H), 7.37 (m, 1H), 7.36 (m, 1H), 7.31 (m, 1H), 7.30 (m 2H), 7.06 (m, 1H), 6.81 (m, 1H), 5.14 (s, 2H). 3.68 (m, 2H), 3.62 (m, 2H), 1.17 (m, 1H), 0.48 (m, 2H), 0.36 (m, 2H)

Example 3—Synthesis of Compound 003

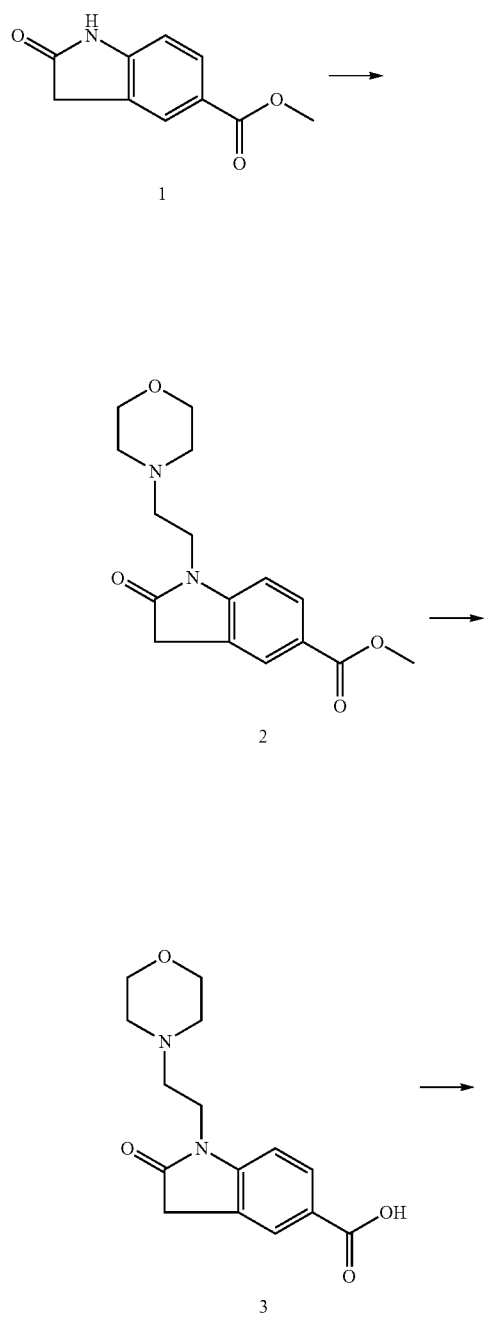

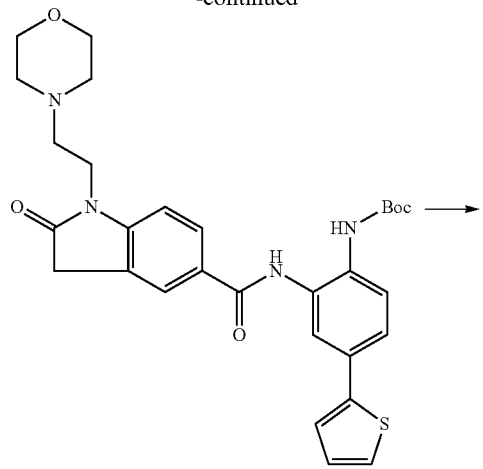

Step 1:

To a solution of methyl 2-oxoindoline-5-carboxylate (0.95 g, 5 mmol) and 4-(2-chloroethyl)morpholine (1.16 g, 6 mmol) in CH$_3$CN (20 mL) was added K$_2$CO$_3$ (1.38 g, 10 mmol) at rt. The reaction mixture was stirred at 75° C. for 5 h. The reaction mixture was cooled and ice water was added. The crude mixture was extracted with EA/water. The EA layer was collected and purified on combiflash with DCM/MeOH (0-10%) to afford Compound 2 as purple solid (0.9 g, 60%).

Step 2:

Compound 2 (608 mg, 2 mmol) was added into 2M HCl (10 mL), the mixture was heated to 100° C. for 6 h. When the reaction was complete, the mixture was concentrated for next step (570 mg, 98%).

Step 3:

To a solution of compound 3 (290 mg, 1 mol) and tert-butyl 3-aminobiphenyl-4-ylcarbamate (255 mg, 0.9 mmol) in Py (10 mL) was added EDCI (382 mg, 2 mmol). The mixture was stirred at rt overnight. The reaction mixture was concentrated to get a residue, and extracted with EA/water. The organic layer was separated, dried and purified on combiflash to afford compound 4 (392 mg, 70%) as a purple oil.

Step 4:

Compound 4 (392 mg, 0.7 mmol) and TFA (1.5 mL) were combined in DCM (5 mL). The reaction was stirred at rt for 0.5 h. The mixture was purified by Prep-HPLC (acid condition) to obtain Compound 003 (80 mg, 25%) as a white solid. LCMS: m/z=463 (M+H)+. $^1$H NMR (400 MHz, DMSO) δ 9.67 (s, 1H), 7.96 (d, J=18.5 Hz, 2H), 7.46 (d, J=2.1 Hz, 1H), 7.36 (dd, J=5.1, 1.1 Hz, 1H), 7.30 (dd, J=8.3, 2.1 Hz, 1H), 7.25 (dd, J=3.6, 1.1 Hz, 1H), 7.19 (s, 1H), 7.06 (dd, J=5.1, 3.6 Hz, 1H), 6.82 (d, J=8.3 Hz, 1H), 5.14 (s, 2H), 3.86 (s, 2H), 3.67 (s, 3H), 3.54 (s, 4H), 3.34 (s, 8H), 5.72-0.52 (m, 41H), 2.48-2.38 (m, 2H).

Example 4—Synthesis of Compound 004

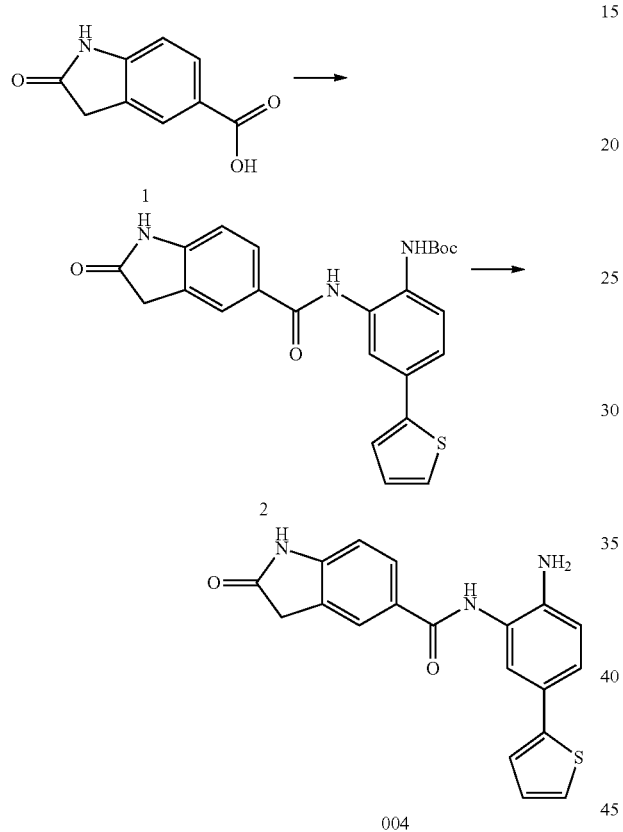

Step 1:

To a solution of compound 1 (177 mg, 05 mmol) in Py (5 mL) was added EDCI (382 mg, 1 mmol) followed by amine tert-butyl 2-amino-4-(thiophen-2-yl)phenylcarbamate (260 mg, 0.9 eq). The mixture was stirred at rt overnight. The reaction was concentrated to get a residue, which was extracted with EA/water to get compound 2 (218 mg, 62%).

Step 2:

Compound 2 (218 mg, 0.62) and TFA (1 mL) were combined in DCM (2 mL), and the reaction was stirred at rt for 1 h. The mixture was concentrated to get a compound 004 (138 mg, 82%) as yellow solid. LCMS: m/z=350 (M+H). $^1$H NMR (400 MHz, DMSO) δ 9.65 (s, 1H), 8.21 (s, 1H), 7.97 (d, J=8.2 Hz, 1H), 7.93 (s, 1H), 7.61 (d, J=1.1 Hz, 1H), 7.52 (d, J=1.8 Hz, 1H), 7.33 (dd, J=8.4, 1.9 Hz, 1H), 7.11 (d, J=8.2 Hz, 1H), 6.82 (d, J=8.4 Hz, 1H), 6.61 (d, J=3.2 Hz, 1H), 6.51 (dd, J=3.2, 1.8 Hz, 1H), 5.14 (s, 2H), 3.64 (d, J=8.1 Hz, 2H).

Example 5—Synthesis of Compound 006

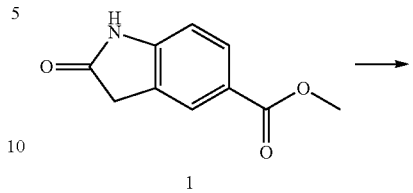

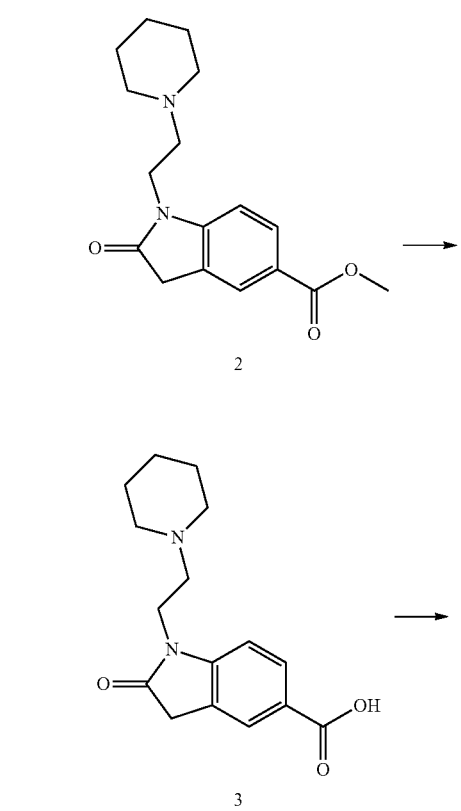

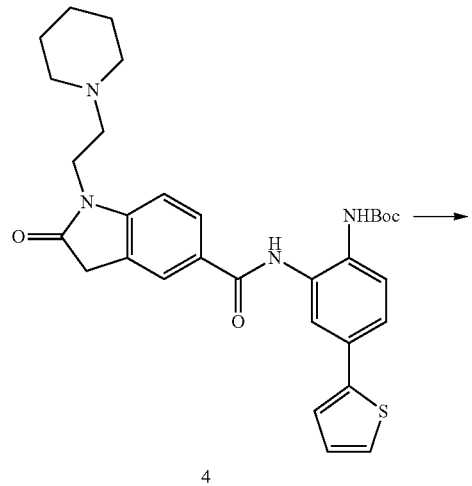

-continued

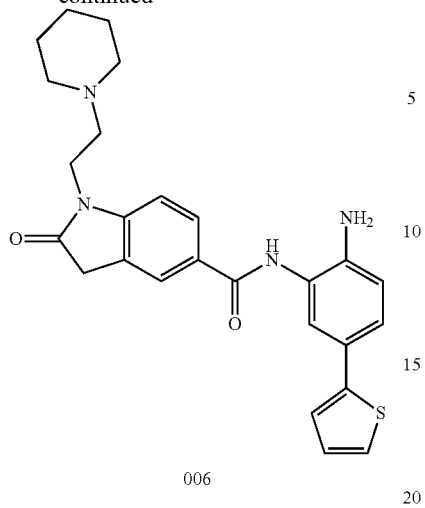

006

Step 1:

Compound 1 (200 mg, 1 mmol), 1-(2-chloroethyl) piperidine (183 mg, 1 mmol), and KOH (112 mg, 2 mmol) were combined in $CH_3CN$ (5 mL). The reaction was stirred at 50° C. for 1 h. After completed, the mixture was concentrated and purified by column chromatography (DCM/MeOH=10/1). Compound 2 was afforded as a purple oil (100 mg, 32%).

Step 2:

Compound 2 (100 mg, 0.33 mmol) was dissolved in HCl (2N in water). The reaction mixture was refluxed for 4 h. The mixture was concentrated for next step (100 mg, crude).

Step 3:

Compound 3 (100 mg, 0.35 mmol), tert-butyl 2-amino-4-(thiophen-2-yl)phenylcarbamate (81 mg, 0.28 mmol), EDCI (202 mg, 1.05 mmol) were combined in Py (5 mL). The reaction was stirred at rt for 3 h. After completed, the mixture was concentrated and purified by column chromatography (DCM/MeOH=10/1). Colorless oil was afforded as compound 4 (40 mg, 20%).

Step 4:

Compound 4 (40 mg, 0.07 mmol) was dissolved in DCM (4 ml). Then TFA (2 ml) was added. The mixture was stirred at rt for 2 h. The crude reaction was concentrated and washed by $Et_2O$. Pink solid was afforded to obtain compound 006 (45 mg, TFA salt). LCMS: m/z=461.1 $(M+H)^+$.
$^1$H NMR (400 MHz, $D_2O$) δ 7.87 (d, J=8.0 Hz, 1H), 7.80 (s, 1H), 7.56 (d, J=6.7 Hz, 1H), 7.42 (s, 1H), 7.37 (d, J=4.9 Hz, 1H), 7.32 (d, J=3.5 Hz, 1H), 7.22 (d, J=8.6 Hz, 1H), 7.07 (dd, J=12.9, 6.6 Hz, 2H), 4.08 (t, J=6.1 Hz, 2H), 3.58 (t, J=12.4 Hz, 4H), 3.34 (t, J=6.3 Hz, 2H), 2.92 (t, J=11.2 Hz, 2H), 1.88 (d, J=15.0 Hz, 2H), 1.78-1.58 (m, 3H), 1.41 (d, J=12.5 Hz, 1H).

Example 6—Synthesis of Compound 007

1

2

3

4

5

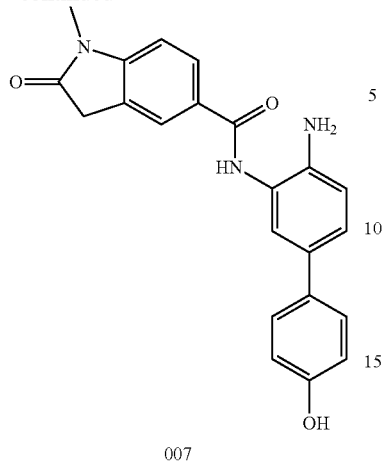

Step 1:

To a solution of tert-butyl 4-bromo-2-nitrophenylcarbamate (634 mg, 2 mmol) and 4-hydroxyphenylboronic acid (276 mg, 2 mmol) in dioxane and water (10 mL:5 ml, v:v=1) was added $K_2CO_3$ (552 mg, 4 mmol) and $Pd(PPh_3)_4$ (231 mg, 0.1 eq). The mixture was stirred at 100° C. overnight. The mixture was then extracted with EA/water. The organic layer was separated, dried, and purified on combiflash (PE/EA=3) to afford compound 2 (462 mg, 70%) as a brown solid.

Step 2:

NaH (85 mg, 2.125 mmol, 60%) was slowly added to a solution of compound 2 (280 mg, 0.85 mol) in dry DMF (10 mL). After the reaction stirred for 5 min, methylsulfamoyl chloride (130 mg, 0.1 eq) was added into the reaction. The mixture was stirred at rt for overnight. The mixture was extracted with EA/water. The organic layer was separated, dried and concentrated to afford compound 3 (350 mg, crude) as a yellow oil.

Step 3:

To a solution of compound 3 (350 mg, crude) in EtOH (10 mL) was added carbol (175 mg, 50% amount) and $FeCl_3$ (14 mg, 0.1 eq) at 60° C. $NH_2$—$NH_2$ (1 mL) was added dropwise, and the mixture was stirred at 60° C. for 30 min. After the reaction had completed, the mixture was filtered. The filtrate was collected and concentrated, washed with water, and the solid was dried to afford the amine 4 (280 mg, 80%).

Step 4:

1-Methyl-2-oxoindoline-5-carboxylic acid (136 mg, 0.7 mmol) was dissolved in Py (10 mL). EDCI (286 mg, 1.5 mmol) was added, followed by amine 4 (280 mg, crude). The mixture was stirred at rt overnight. The reaction mixture was concentrated, diluted with water, and the precipitate was collected to afford the crude solid 5 (300 mg, crude).

Step 5:

The crude material of compound 5 (100 mg, crude) and TFA (1 mL) were combined in DCM (2 mL). The reaction was stirred at rt for 1 h. The mixture was concentrated and purified on prep-HPLC (acid condition) to get a compound 007 (17 mg, 5.4%, 4 steps) as yellow solid. LCMS: m/z=374 $(M+H)^+$. $^1H$ NMR (400 MHz, DMSO) δ 9.65 (s, 1H), 8.00 (d, J=8.1 Hz, 1H), 7.92 (s, 1H), 7.40 (d, J=2.1 Hz, 1H), 7.36 (d, J=8.6 Hz, 2H), 7.21 (dd, J=8.3, 2.2 Hz, 1H), 7.11 (d, J=8.2 Hz, 1H), 6.83 (d, J=8.3 Hz, 1H), 6.78 (d, J=8.6 Hz, 2H), 4.94 (s, 2H), 3.65 (s, 2H), 3.18 (s, 3H).

Example 7—Synthesis of Compound 009

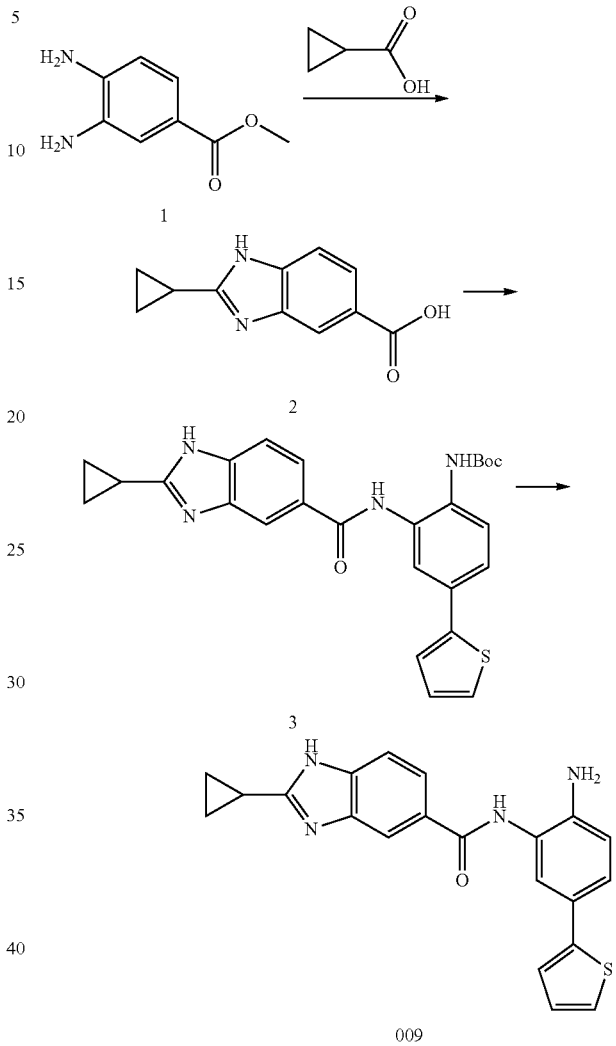

Step 1:

Compound 1 (830 mg, 5 mmol) and cyclopropanecarboxylic acid (430 mg, 5 mmol) were combined in 4M HCl (20 mL). The reaction was refluxed overnight. After completed, the mixture was concentrated and purified by Prep-HPLC. White solid was afforded as Compound 2 (312 mg, 31%).

Step 2:

Compound 2 (100 mg, 0.50 mmol), tert-butyl 2-amino-4-(thiophen-2-yl)phenylcarbamate (144 mg, 0.50 mmol), and EDCI (288 mg, 1.50 mmol) were combined in Py (5 mL). The reaction was stirred at rt overnight. After completed, the mixture was concentrated and purified by column chromatography (DCM/MeOH=10/1). Compound 3 was isolated as a colorless oil (54 mg, 23%).

Step 3:

Compound 3 (54 mg, 0.11 mmol) was dissolved in DCM (2 ml). Then TFA (1 ml) was added. The mixture was stirred at rt for 2 h. The crude material was concentrated and washed with $Et_2O$. Compound 009 was isolated as a white solid (30 mg, TFA salt). LCMS: m/z=375.0 $(M+H)^+$. $^1H$ NMR (400 MHz, DMSO) δ 9.96 (s, 1H), 8.26 (s, 1H), 8.07 (d, J=8.0 Hz, 1H), 7.76 (d, J=8.5 Hz, 1H), 7.50 (s, 1H), 7.35

(dd, J=8.5, 2.5 Hz, 2H), 7.28 (d, J=3.0 Hz, 1H), 7.07 (t, J=3.5 Hz, 1H), 6.88 (s, 1H), 2.42 (t, J=3.0 Hz, 1H), 1.37 (dd, J=2.5 Hz, 4H).

Example 8—Synthesis of Compound 010

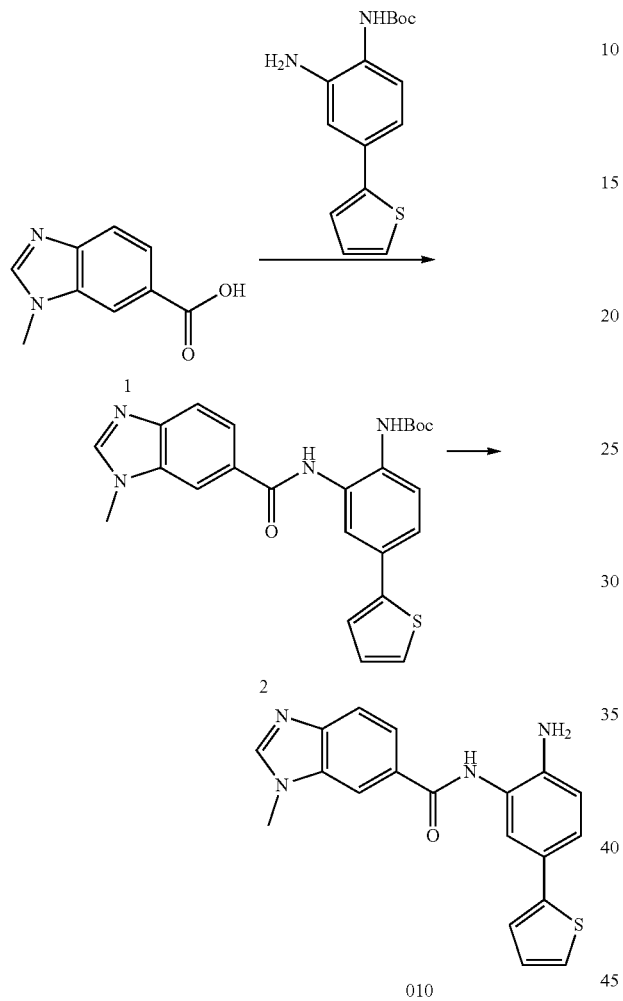

Step 1:
Compound 1 (50 mg, 0.28 mmol), tert-butyl 2-amino-4-(thiophen-2-yl)phenylcarbamate (66 mg, 0.23 mmol), and EDCI (164 mg, 0.85 mmol) were combined in Py (3 mL). The reaction was stirred at rt overnight. After completed, the mixture was concentrated and washed with water and ether. The white solid was afforded as Compound 2 (100 mg, 72%).

Step 2:
Compound 2 (100 mg, 0.22 mmol) and TFA (2 mL) were combined in DCM (4 mL) and stirred at rt for 2 h. The mixture was concentrated and purified by Prep-HPLC (base method). White solid was afforded to obtain compound 010 (56 mg, 72%). LCMS: m/z=349.1 (M+H)+. $^1$H NMR (400 MHz, DMSO) δ 9.80 (s, 1H), 8.36 (s, 1H), 8.31 (d, J=1.1 Hz, 1H), 7.90 (dd, J=8.5, 1.6 Hz, 1H), 7.74 (d, J=8.5 Hz, 1H), 7.51 (d, J=2.1 Hz, 1H), 7.37 (dd, J=5.1, 1.0 Hz, 1H), 7.32 (dd, J=8.3, 2.2 Hz, 1H), 7.26 (dd, J=3.6, 1.1 Hz, 1H), 7.06 (dd, J=5.1, 3.6 Hz, 1H), 6.84 (d, J=8.3 Hz, 1H), 5.18 (s, 2H), 3.93 (s, 3H).

Example 9—Synthesis of Compound 011

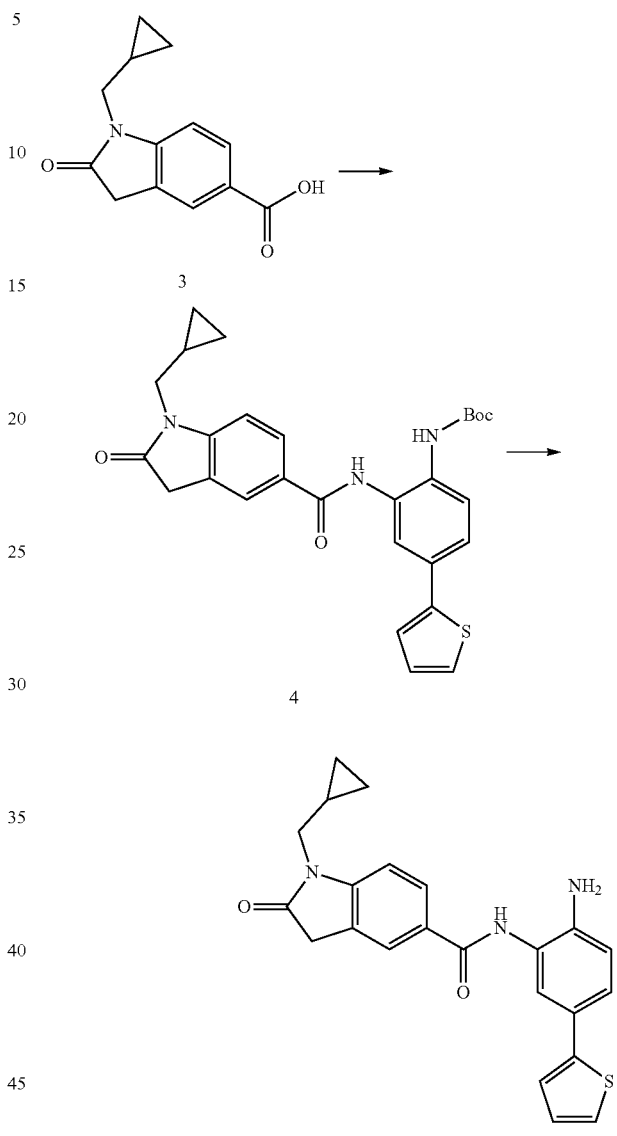

Step 1:
Compound 3 (231 mg, 1 mmol), amine tert-butyl 2-amino-4-(thiophen-2 yl)phenylcarbamate (290 mg, 1 mmol), and EDCI (382 mg, 2 mmol) were combined in Py (5 mL). The reaction was stirred at rt overnight. The mixture was concentrated to get a residue, which was purified by silica gel to get compound 4 (302 mg, 60%) as yellow solid.

Step 2:
Compound 4 (252 mg, 0.5 mmol) and TFA (1 mL) were combined in DCM (2 mL). The reaction was stirred at rt for 1 h. The mixture was concentrated to get a compound 011 (161, 80%) as yellow solid. LCMS: m/z=404 (M+H)+. $^1$H NMR (400 MHz, DMSO) δ 9.66 (s, 1H), 8.00 (m, 1H), 7.93 (s, 1H), 7.46 (s, 1H), 7.36 (m, 1H), 7.31 (m, 1H), 7.30 (m 2H), 7.06 (m, 1H), 6.81 (m, 1H), 5.14 (s, 2H). 3.68 (m, 2H), 3.62 (m, 2H), 1.17 (m, 1H), 0.48 (m, 2H), 0.36 (m, 2H)

Example 10—Synthesis of Compound 012

Example 11—Synthesis of Compound 013

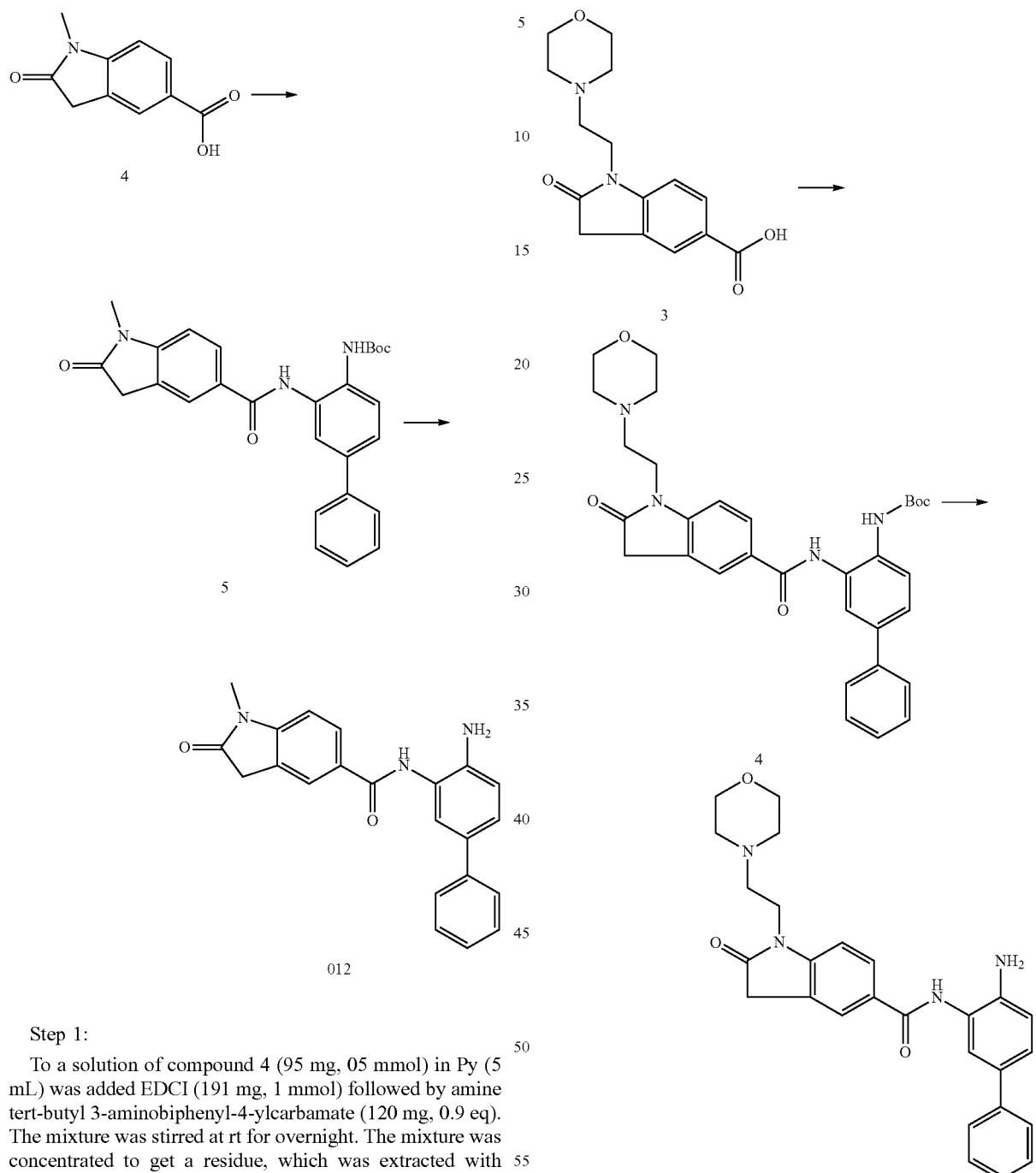

Step 1:

To a solution of compound 4 (95 mg, 05 mmol) in Py (5 mL) was added EDCI (191 mg, 1 mmol) followed by amine tert-butyl 3-aminobiphenyl-4-ylcarbamate (120 mg, 0.9 eq). The mixture was stirred at rt for overnight. The mixture was concentrated to get a residue, which was extracted with EA/water to get compound 5 (220 mg, crude).

Step 2:

Compound 5 (220 mg, crude) and TFA (1 mL) were combined in DCM (2 mL). The reaction was stirred at rt for 1 h. The mixture was concentrated to get a Compound 012 (25, 16%) as yellow solid. LCMS: m/z=368 (M+H)+. $^1$H NMR (400 MHz, DMSO) δ 9.65 (s, 1H), 7.61 (d, J=1.1 Hz, 1H), 7.52-7.41 (m, 5H), 7.33 (dd, J=8.4, 1.9 Hz, 1H), 7.11 (d, J=8.2 Hz, 1H), 6.82 (d, J=8.4 Hz, 1H), 6.61 (d, J=3.2 Hz, 1H), 6.51 (dd, J=3.2, 1.8 Hz, 1H), 5.14 (s, 2H), 3.64 (d, J=8.1 Hz, 2H), 3.17 (d, J=10.2 Hz, 3H).

Step 1:

To a solution of compound 3 (290 mg, 1 mmol) and tert-butyl 3-aminobiphenyl-4-ylcarbamate (255 mg, 0.9 mmol) in Py (10 mL) was added EDCI (382 mg, 2 mmol). The mixture was stirred at rt overnight. The mixture was concentrated to get a residue and extracted with EA/water. The organic layer was separated, dried, and purified on combiflash to afford compound 4 (376 mg, 68%) as a purple oil.

Step 2:

Compound 4 (376 mg, 0.68 mmol) and TFA (1.5 mL) were combined in DCM (5 mL). The reaction was stirred at rt for 0.5 h. The mixture was purified by Prep-HPLC (acid condition) to obtain compound 013 (100 mg, 32%) as a white solid. LCMS: m/z=457 (M+H)+. 1H NMR (400 MHz, DMSO) δ 9.67 (s, 1H), 7.56-7.49 (m, 4H), 7.47 (d, J=8, 1H), 7.36 (dd, J=5.1, 1.1 Hz, 1H), 7.30 (dd, J=8.3, 2.1 Hz, 1H), 7.26 (dd, J=3.6, 1.1 Hz, 1H), 7.20 (s, 1H), 7.06 (dd, J=5.1, 3.6 Hz, 1H), 6.82 (d, J=8.3 Hz, 1H), 5.14 (s, 2H), 3.86 (s, 2H), 3.67 (s, 3H), 3.54 (s, 4H), 3.34 (s, 8H), 5.72-0.52 (m, 41H), 2.48-2.38 (m, 2H).

Example 12—Synthesis of Compound 014

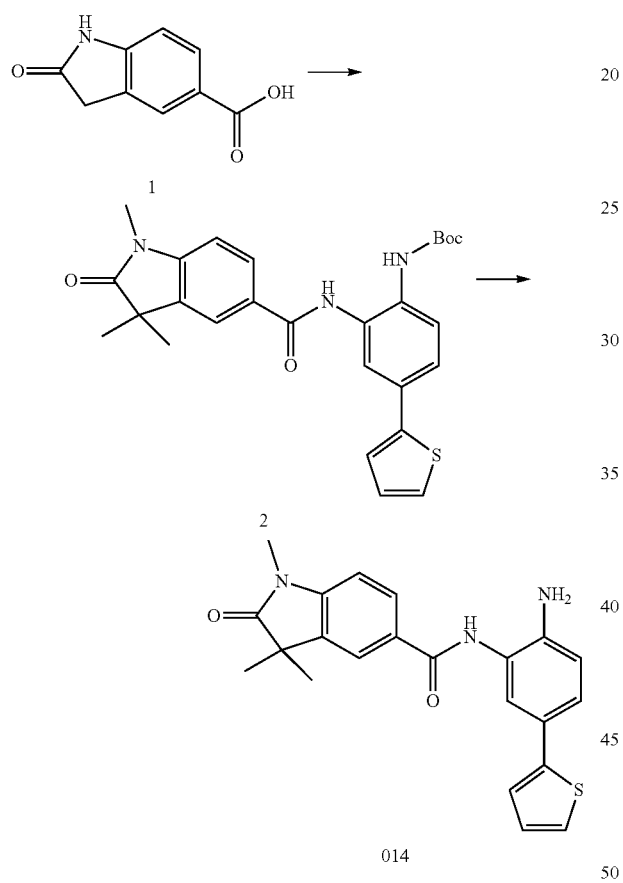

Step 1:

Compound 1 (177 g, 1 mmol), iodomethane (426 mg, 3 mmol), and NaH (60%, 160 mg, 4 mmol) were combined in THF (5 mL). The reaction mixture was stirred at 60° C. for 3 h. The mixture was concentrated to get a residue The crude residue was dissolved in Py (5 mL). tert-Butyl 2-amino-4-(thiophen-2-yl)phenylcarbamate (290 mg, 1 mmol) and EDCI (382 mg, 2 mmol) were added and the reaction was stirred at rt overnight. The mixture was concentrated to get a residue, which was purified by silica gel to get compound 2 (246 mg, 50%, 2 steps) as yellow solid.

Step 2:

Compound 2 (246 mg, 0.5 mmol) and TFA (1 mL) were combined in DCM (2 mL), and the reaction was stirred at rt overnight. The mixture was concentrated to get compound 014 (156 mg, 80%) as yellow solid. LCMS: m/z=492 (M+H)+. 1H NMR (400 MHz, DMSO) δ 9.88 (s, 1H), 8.02 (d, J=8.0 Hz, 2H), 7.53 (s, 1H), 7.42 (t, J=7.5 Hz, 2H), 7.34 (d, J=3.4 Hz, 1H), 7.17 (d, J=8.2 Hz, 1H), 7.09 (d, J=4.3 Hz, 1H), 6.99 (d, J=8.3 Hz, 1H), 3.21 (s, 3H), 1.34 (s, 6H).

Example 13—Synthesis of Compound 015

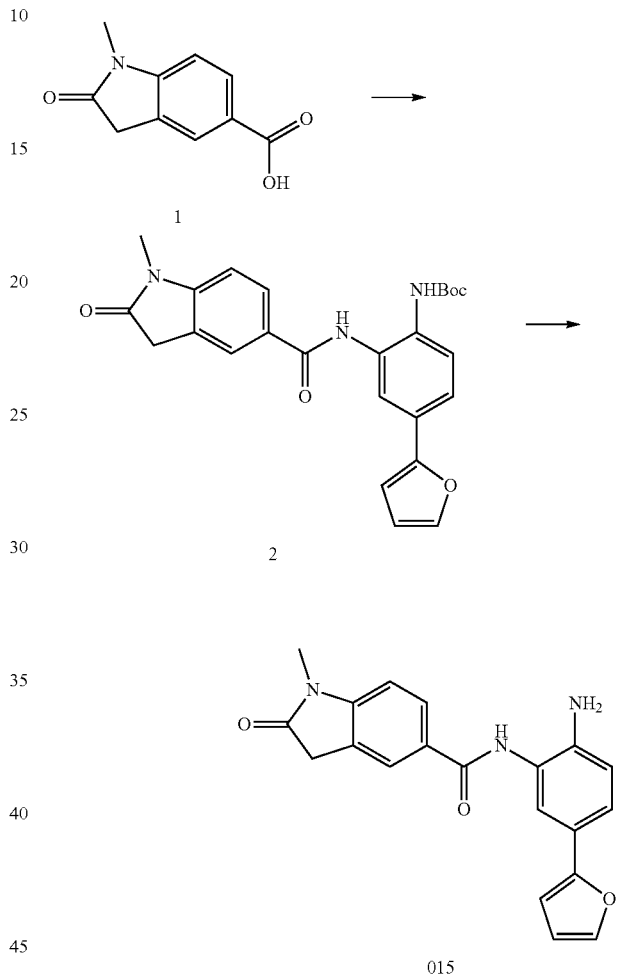

Step 1:

To a solution of compound 1 (95 mg, 05 mmol) in Py (5 mL) was added EDCI (191 mg, 1 mmol) followed by amine tert-butyl 2-amino-4-(furan-2-yl)phenylcarbamate (123 mg, 0.9 eq). The mixture was stirred at rt overnight. The mixture was concentrated to get a residue, which was extracted with EA/water to get compound 2 (226 mg, crude).

Step 2:

Compound 2 (225 mg, crude) and TFA (1 mL) were combined in DCM (2 mL) and the reaction was stirred at rt for 1 h. The mixture was concentrated to get a compound 015 (20 mg, 13%, 2 steps) as yellow solid. LCMS: m/z=348 (M+H). 1H NMR (400 MHz, DMSO) δ 9.65 (s, 1H), 8.01 (d, J=8.2 Hz, 1H), 7.93 (s, 1H), 7.61 (d, J=1.1 Hz, 1H), 7.52 (d, J=1.8 Hz, 1H), 7.33 (dd, J=8.4, 1.9 Hz, 1H), 7.11 (d, J=8.2 Hz, 1H), 6.82 (d, J=8.4 Hz, 1H), 6.61 (d, J=3.2 Hz, 1H), 6.51 (dd, J=3.2, 1.8 Hz, 1H), 5.14 (s, 2H), 3.64 (d, J=8.1 Hz, 2H), 3.17 (d, J=10.2 Hz, 3H).

Example 14—Synthesis of Compound 016

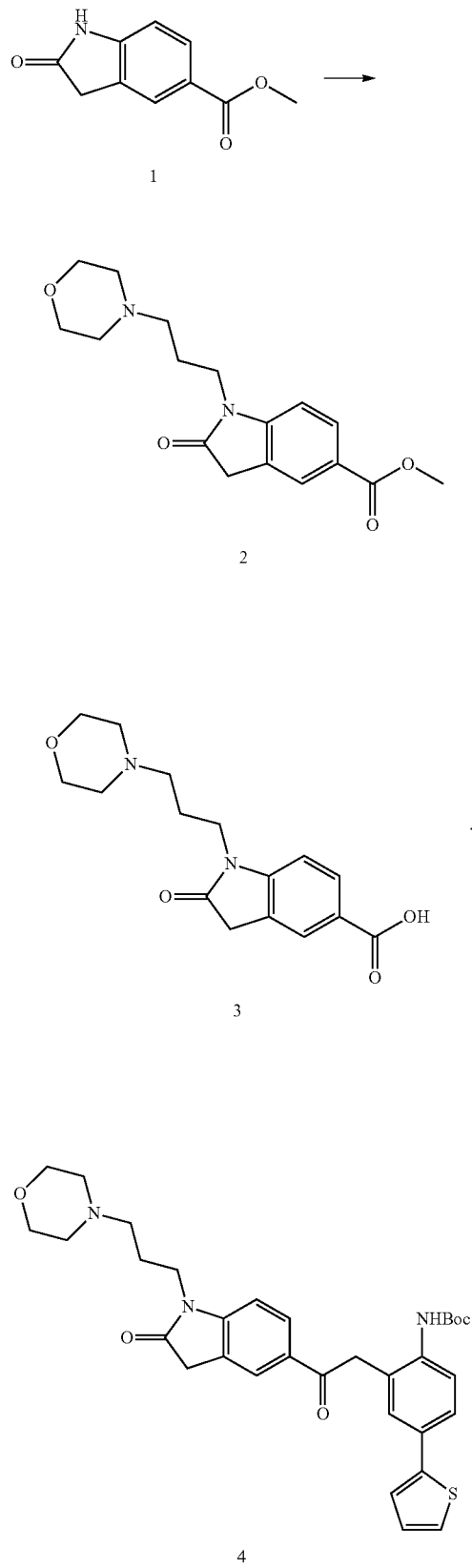

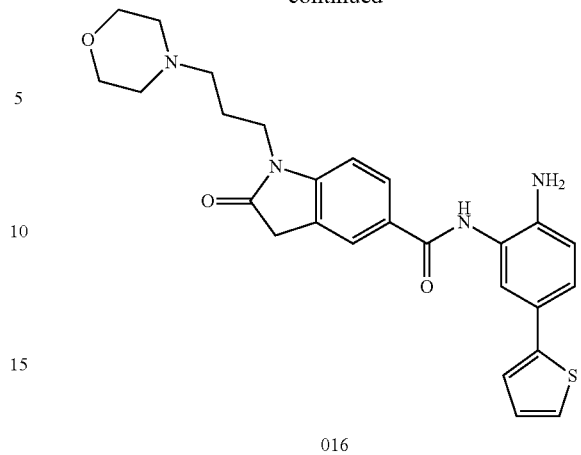

016

Step 1:

Compound 1 (191 mg, 1 mmol), 4-(3-chloropropyl) morpholine (163 mg, 1 mmol), and $K_2CO_3$ (276 mg, 2 mmol) were combined in $CH_3CN$ (5 mL), and the reaction was stirred at 80° C. for 2 h. After completed, the mixture was concentrated and purified by column chromatography (DCM/MeOH=10/1). Purple oil was afforded as Compound 2 (260 mg, crude).

Step 2:

Compound 2 (200 mg, crude) was dissolved in HCl (2N in water). The reaction was stirred at 100° C. for 3 h. The mixture was concentrated for next step (200 mg, crude).

Step 3:

Compound 3 (200 mg, 0.66 mmol), tert-butyl 2-amino-4-(thiophen-2-yl)phenylcarbamate (154 mg, 0.53 mmol), and EDCI (380 mg, 1.98 mmol) were dissolved in Py (5 mL). The reaction was stirred at rt overnight. After completed, the mixture was concentrated and purified by column chromatography (DCM/MeOH=10/1). Colorless oil was afforded as Compound 4 (290 mg, 77%).

Step 4:

Compound 4 (290 mg, 0.50 mmol) was dissolved in DCM (4 ml). Then TFA (2 ml) was added. The mixture was stirred at rt for 2 h. The reaction was concentrated and washed with $Et_2O$. Pink solid was afforded to obtain compound 016 (200 mg, TFA salt). LCMS: m/z=477.1 (M+H)$^+$. $^1$H NMR (400 MHz, DMSO) δ 9.77 (s, 2H), 8.03 (d, J=8.9 Hz, 1H), 7.97 (s, 1H), 7.49 (d, J=1.9 Hz, 1H), 7.39 (d, J=4.3 Hz, 1H), 7.34 (dd, J=8.3, 2.1 Hz, 1H), 7.28 (d, J=2.6 Hz, 1H), 7.22 (d, J=8.3 Hz, 1H), 7.07 (dd, J=5.0, 3.6 Hz, 1H), 6.89 (d, J=8.3 Hz, 1H), 3.97 (d, J=12.2 Hz, 2H), 3.81 (t, J=6.5 Hz, 2H), 3.68 (s, 2H), 3.61 (d, J=11.5 Hz, 2H), 3.40 (t, J=12.1 Hz, 2H), 3.19 (s, 2H), 3.05 (s, 2H), 2.00 (d, J=9.5 Hz, 2H).

Example 15—Synthesis of Compound 018

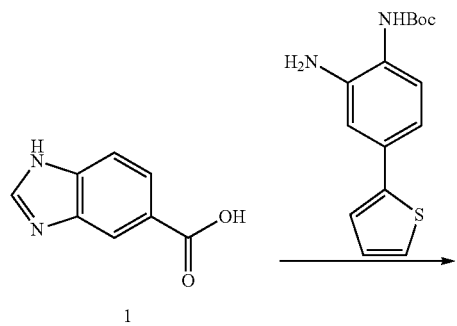

Example 16—Synthesis of Compound 019

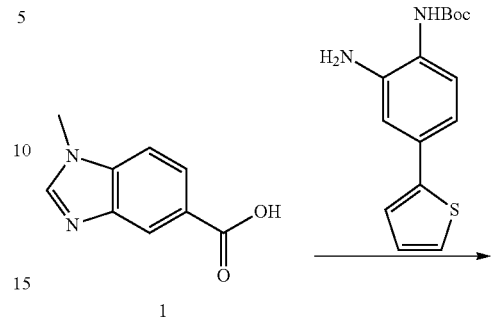

Step 1:

Compound 1 (100 mg, 0.62 mmol), tert-butyl 2-amino-4-(thiophen-2-yl)phenylcarbamate (151 mg, 0.52 mmol), HOAt (141 mg, 1.04 mmol), EDCI (200 mg, 1.04 mmol), and Et$_3$N (0.2 mL) were combined in THF (5 mL), and the reaction was stirred at rt overnight. After completed, the mixture was concentrated and the crude was carried over for next step (300 mg, crude).

Step 2:

The crude Compound 2 (300 mg, crude) and TFA (3 mL) were combined in DCM (6 mL). The reaction was stirred at rt for 2 h. The mixture was purified by Prep-HPLC (base method). White solid was afforded to obtain compound 018 (130 mg, 43%, 2 steps). LCMS: m/z=334.8 (M+H)$^+$. $^1$H NMR (400 MHz, DMSO) δ 9.77 (s, 1H), 8.39 (d, J=33.4 Hz, 2H), 7.90 (d, J=7.6 Hz, 1H), 7.71 (s, 1H), 7.51 (s, 1H), 7.39-7.21 (m, 3H), 7.07 (dd, J=13.2, 9.0 Hz, 1H), 6.83 (d, J=8.2 Hz, 1H).

Step 1:

Compound 1 (100 mg, 0.57 mmol), tert-butyl 2-amino-4-(thiophen-2-yl)phenylcarbamate (139 mg, 0.48 mmol), and EDCI (276 mg, 1.44 mmol) were combined in Py (5 mL), and the reaction was stirred at rt overnight. After completed, the mixture was concentrated and washed with ether (200 mg, 78%).

Step 2:

Compound 2 (200 mg, 0.446 mmol) and TFA (2 mL) were combined in DCM (4 mL). The reaction was stirred at rt for 2 h. The mixture was concentrated and washed with Et$_2$O. White solid was afforded to obtain compound 019 (270 mg, TFA salt). LCMS: m/z=349.1 (M+H). $^1$H NMR (400 MHz, DMSO) δ 10.03 (s, 1H), 9.06 (s, 1H), 8.46 (s, 1H), 8.14 (d, J=8.2 Hz, 1H), 7.93 (d, J=8.6 Hz, 1H), 7.55 (s, 1H), 7.39 (dd, J=14.1, 3.5 Hz, 2H), 7.31 (d, J=3.2 Hz, 1H), 7.13-7.04 (m, 1H), 6.93 (d, J=8.3 Hz, 1H), 4.02 (s, 3H).

Example 17—Synthesis of Compound 020

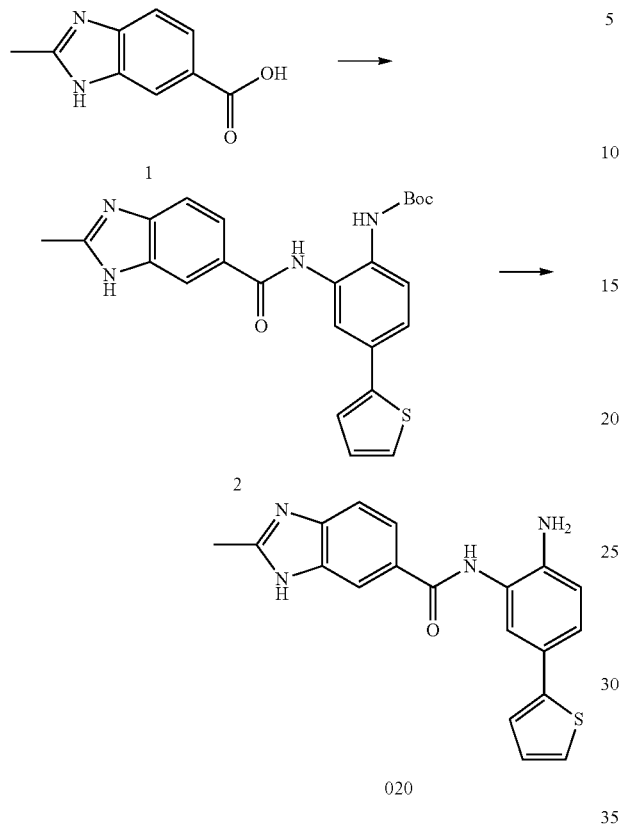

Step 1:
2-Methyl-3H-benzo[d]imidazole-5-carboxylic acid (176 mg, 1 mmol), tert-butyl 2-amino-4-(thiophen-2-yl)phenyl-carbamate (290 mg, 1 mmol) and EDCI (382 mg, 2 mmol) were combined in Py (5 mL), and the reaction was stirred at rt overnight. The mixture was concentrated to get a residue, which was purified by silica gel to get compound 2 (314 mg, 70%) as yellow solid.

Step 2:
Compound 2 (224 mg, 0.5 mmol) and TFA (1 mL) were combined in DCM (2 mL), and the reaction was stirred at rt for 1 h. The mixture was concentrated to get a compound 020 (170 mg, 100%) as yellow solid. LCMS: m/z=349 (M+H)$^+$. $^1$H NMR (400 MHz, DMSO) δ 10.03 (s, 1H), 8.39 (s, 1H), 8.14 (d, J=8.5 Hz, 1H), 7.88 (d, J=8.6 Hz, 1H), 7.51 (s, 1H), 7.43-7.34 (m, 2H), 7.29 (d, J=3.5 Hz, 1H), 7.10-7.04 (m, 1H), 6.89 (d, J=8.4 Hz, 1H), 2.82 (s, 3H).

Examples 18 and 19—Synthesis of Compounds 021 and 022

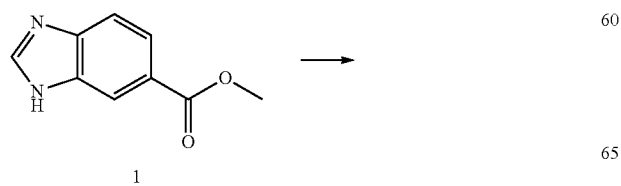

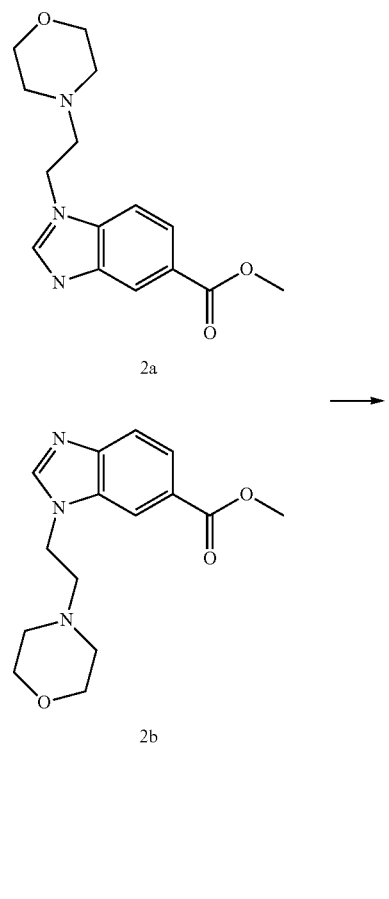

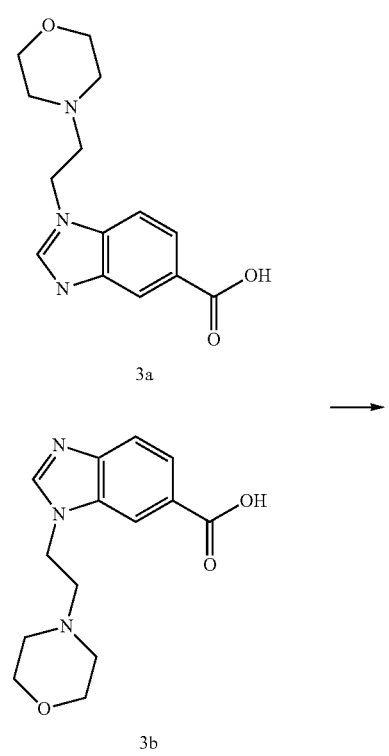

49

-continued

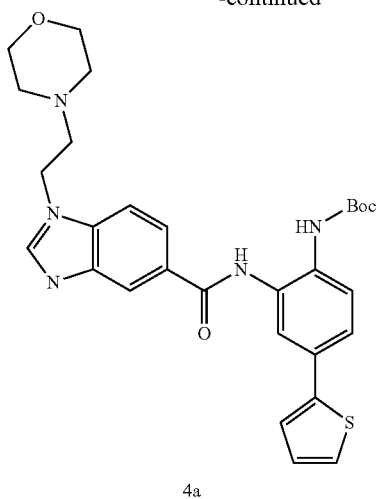

4a

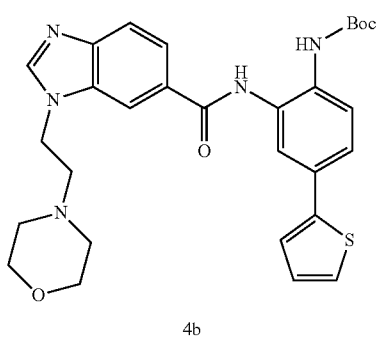

4b

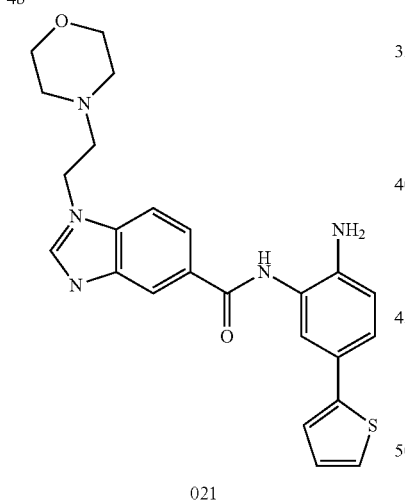

021

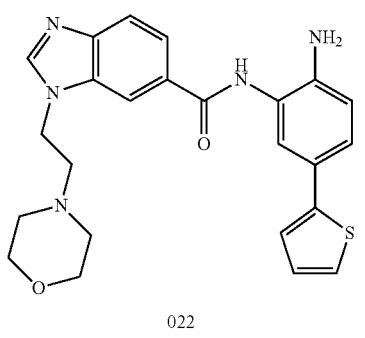

022

50

Step 1:

Compound 1 (352 g, 2 mmol), 4-(2-chloroethyl)morpholine (300 mg, 2 mmol), and $K_2CO_3$ (276 mg, 2 mmol) were combined in DMF (5 mL). The reaction was stirred at rt overnight. The mixture was diluted with EA (300 mL), filtered (flash silica gel), and concentrated to get a residue, which was purified by silica gel to get the mixture of 2a and 2b (231 mg, 40%) as yellow solid.

Step 2:

A mixture of compound 2a and 2b (289 mg, 1 mmol) and LiOH—$H_2O$ (42 mg, 1 mmol) were combined in MeOH (2 mL), and was stirred at 60° C. overnight. The mixture was concentrated. The crude material was combined with tert-butyl 2-amino-4-(thiophen-2-yl)phenylcarbamate (290 mg, 1 mmol) and EDCI (382 mg, 2 mmol) in Py (5 mL), and was stirred at rt overnight. The mixture was concentrated to get a residue, which was purified by silica gel to get the mixture of 4a and 4b (383 mg, 70%) as yellow solid.

Step 3:

A mixture of compound 4a and 4b (274 mg, 0.5 mmol) and TFA (1 mL) were combined in DCM (2 mL) stirred at rt for 1 h. The mixture was concentrated to get a residue, which was purified by chiral HPLC to compound 021 (88 mg, 40%) as yellow solid. LCMS: m/z=442 (M+H)$^+$. $^1$H NMR (500 MHz, DMSO) δ 9.79 (s, 1H), 8.39 (s, 1H), 8.35 (s, 1H), 7.93 (m, 1H), 7.95-7.94 (m, 1H), 7.58-7.56 (m, 3H), 7.41-7.38 (m, 2H), 7.35-7.32 (m, 1H), 7.25 (m, 1H), 6.89-6.88 (m, 1H), 5.120 (s, 2H), 4.43-4.41 (m, 2H), 3.53-3.51 (m, 4H), 2.72-2.71 (m, 2H), 2.46 (m, 4H). Compound 022 (88 mg, 40%). LCMS: m/z=442 (M+H)$^+$. $^1$H NMR (500 MHz, DMSO) δ 1H NMR (500 MHz, DMSO) δ 9.76 (s, 1H), 8.40 (s, 1H), 8.367 (s, 1H), 7.93 (m, 1H), 7.95-7.94 (m, 1H), 7.58-7.56 (m, 3H), 7.41-7.38 (m, 2H), 7.35-7.32 (m, 1H), 7.25 (m, 1H), 6.89-6.88 (m, 1H), 5.120 (s, 2H), 4.43-4.41 (m, 2H), 3.53-3.51 (m, 4H), 2.72-2.71 (m, 2H), 2.46 (m, 4H).

Example 20—Synthesis of Compound 024

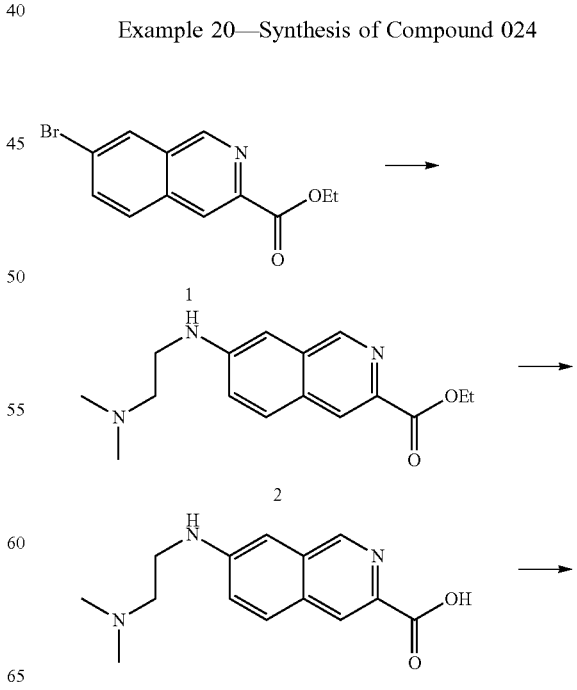

(s, 1H), 8.74 (s, 1H), 7.88 (d, J=8.5, 1H), 7.53 (s, 1H), 7.38 (d, J=8.0, 2H), 7.32 (d, J=8.5, 1H), 7.26 (s, 1H), 7.06 (s, 2H), 6.84 (d, J=8.5, 1H), 5.13 (s, 2H), 3.27 (t, 2H), 2.52 (t, 2H), 2.17 (s, 6H).

Example 21—Synthesis of Compound 025

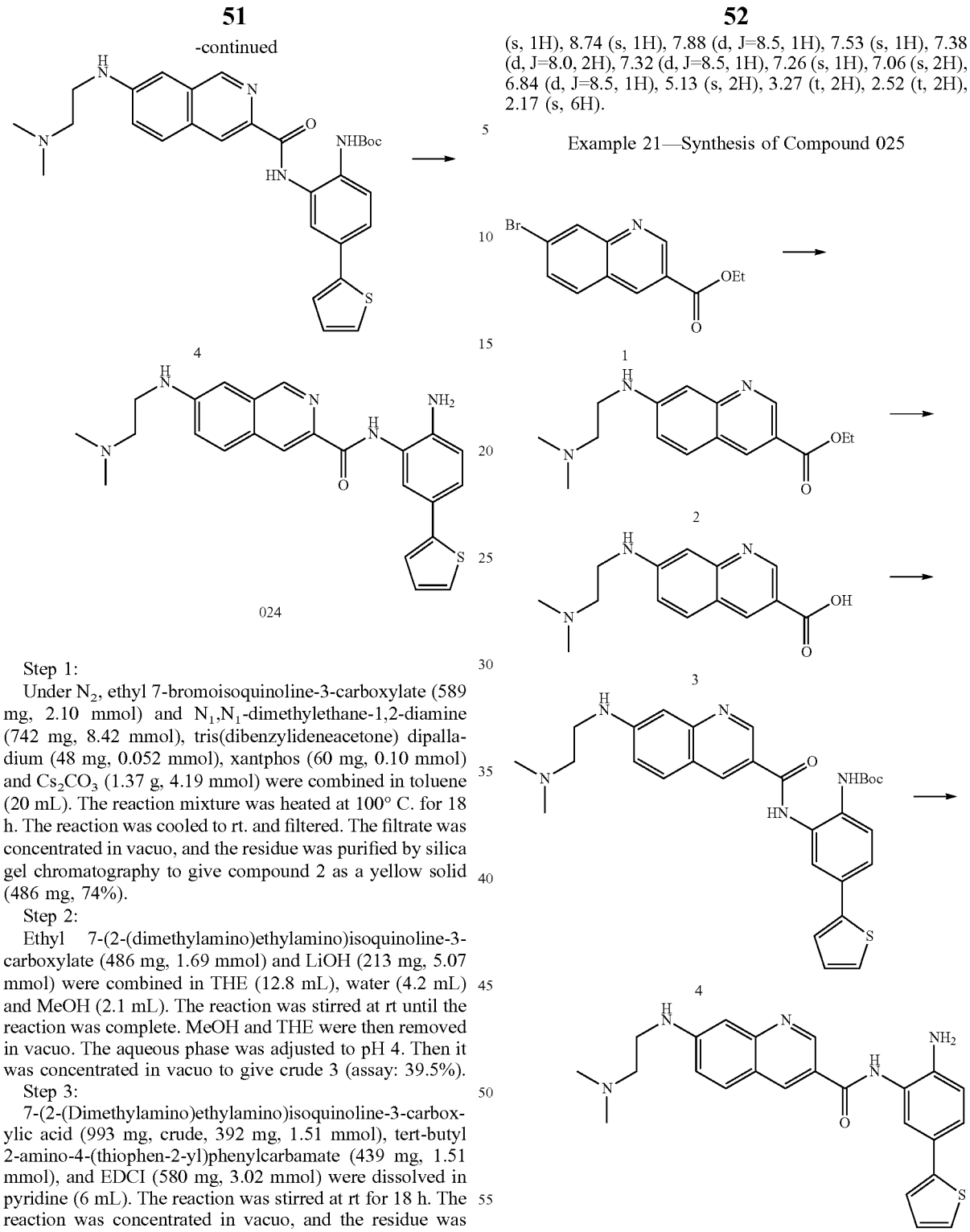

Step 1:

Under N₂, ethyl 7-bromoisoquinoline-3-carboxylate (589 mg, 2.10 mmol) and N₁,N₁-dimethylethane-1,2-diamine (742 mg, 8.42 mmol), tris(dibenzylideneacetone) dipalladium (48 mg, 0.052 mmol), xantphos (60 mg, 0.10 mmol) and Cs₂CO₃ (1.37 g, 4.19 mmol) were combined in toluene (20 mL). The reaction mixture was heated at 100° C. for 18 h. The reaction was cooled to rt. and filtered. The filtrate was concentrated in vacuo, and the residue was purified by silica gel chromatography to give compound 2 as a yellow solid (486 mg, 74%).

Step 2:

Ethyl 7-(2-(dimethylamino)ethylamino)isoquinoline-3-carboxylate (486 mg, 1.69 mmol) and LiOH (213 mg, 5.07 mmol) were combined in THF (12.8 mL), water (4.2 mL) and MeOH (2.1 mL). The reaction was stirred at rt until the reaction was complete. MeOH and THF were then removed in vacuo. The aqueous phase was adjusted to pH 4. Then it was concentrated in vacuo to give crude 3 (assay: 39.5%).

Step 3:

7-(2-(Dimethylamino)ethylamino)isoquinoline-3-carboxylic acid (993 mg, crude, 392 mg, 1.51 mmol), tert-butyl 2-amino-4-(thiophen-2-yl)phenylcarbamate (439 mg, 1.51 mmol), and EDCI (580 mg, 3.02 mmol) were dissolved in pyridine (6 mL). The reaction was stirred at rt for 18 h. The reaction was concentrated in vacuo, and the residue was purified by reverse phase chromatography to give compound 4 (711 mg, 79%).

Step 4:

tert-Butyl-2-(7-(2-(dimethylamino)ethylamino)isoquinoline-3-carboxamido)-4-(thiophen-2-yl)phenylcarbamate (711 mg) was dissolved in DCM (4 mL) TFA (4 mL) was added at 0° C. The reaction was stirred at 0° C. to rt for 2 h. The reaction mixture was concentrated in vacuo, and the residue was purified by prep-HPLC to give product 024 as an off-white solid (386.4 mg, 67%). LCMS: m/z=432.1 (M+H)⁺. ¹H-NMR (400 MHz, DMSO) δ 9.84 (s, 1H), 9.21

Step 1:

Under N₂, ethyl 7-bromoquinoline-3-carboxylate (1.00 g, 3.57 mmol), N,N-dimethylethane-1,2-diamine (346 mg, 3.93 mmol), tris(dibenzylideneacetone) dipalladium (82 mg, 0.089 mmol), Ruphos (83 mg, 0.18 mmol) and Cs₂CO₃ (2.33 g, 7.14 mmol) were combined in toluene (40 mL). The reaction was heated at 100° C. and stirred for 18 h. The reaction was then was cooled to rt. and filtered. The filtrate was concentrated in vacuo, and the residue was purified by reverse phase chromatography to give compound 2 as an oil (665 mg, 65%).

Step 2:

Ethyl 7-(2-(dimethylamino)ethylamino)quinoline-3-carboxylate (665 mg, 2.31 mmol) and LiOH (292 mg, 6.94 mmol) were combined in THF (17.6 mL), water (5.8 mL) and MeOH (2.9 mL). The reaction was stirred at rt until completed. MeOH and THF were then removed in vacuo. The aqueous phase was adjusted to pH 7 and concentrated in vacuo to give crude 3.

Step 3:

7-(2-(Dimethylamino)ethylamino)quinoline-3-carboxylic acid (20 mg, 0.077 mmol), EDCI (18 mg, 0.093 mmol), and HOAT (12 mg, 0.085 mmol) were combined in DIPEA (25.5 mL, 0.154 mmol). The reaction was stirred at rt for 10 min, then tert-butyl 2-amino-4-(thiophen-2-yl)phenyl carbamate (22 mg, 0.077 mmol) was added. The reaction was heated to 50° C. and stirred for 16 h. The crude material was purified by reverse phase column chromatography to give compound 4.

Step 4:

tert-Butyl 2-(7-(2-(dimethylamino)ethylamino)quinoline-3-carboxamido)-4-(thiophen-2-yl)phenylcarbamate (377 mg, 0.71 mmol) was dissolved in DCM (4 mL). TFA (2 mL) was added at 0° C. The reaction mixture was stirred at 0° C. to rt. for 2 h. The crude reaction was concentrated in vacuo, and the residue was purified by prep-HPLC to give product 025 as a yellow solid (111 mg, 36%). LCMS: m/z=432.1 (M+H)+. ¹H-NMR (400 MHz, DMSO) δ 9.84 (s, 1H), 9.21 (s, 1H), 8.74 (s, 1H), 7.88 (d, J=8.5, 1H), 7.53 (s, 1H), 7.38 (d, J=8.0, 2H), 7.32 (d, J=8.5, 1H), 7.26 (s, 1H), 7.06 (s, 2H), 6.84 (d, J=8.5, 1H), 5.22 (s, 2H), 3.28 (t, 2H), 2.54 (t, 2H), 2.23 (s, 6H).

Example 22—Synthesis of Compound 026

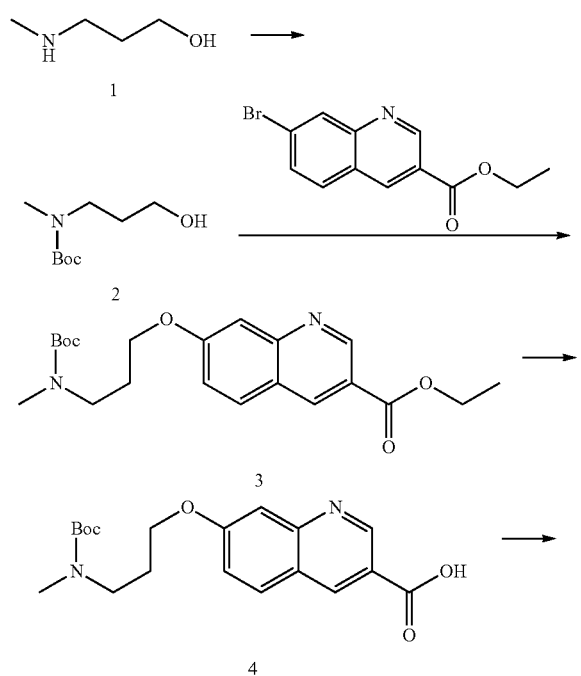

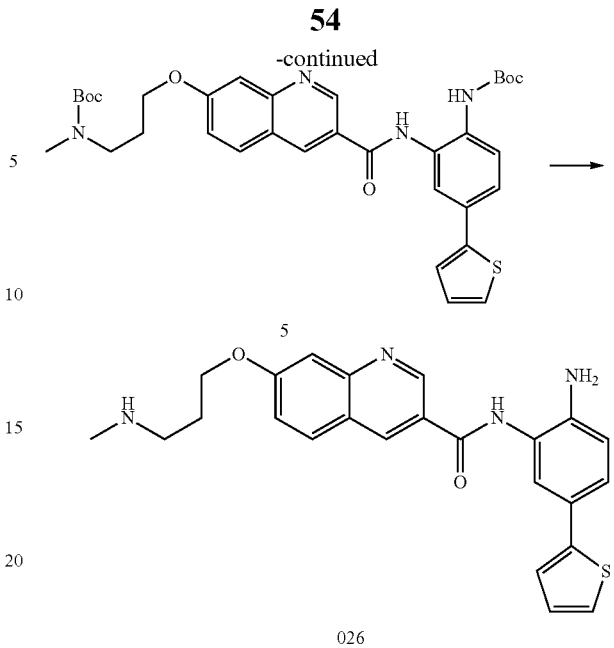

Step 1:

3-(Methylamino)propan-1-ol (8.9 g, 100 mmol), Boc₂O (21.8 g, 100 mmol), and Et₃N (10.1 g, 100 mmol) were combined in DCM (200 mL). The reaction was stirred at rt overnight. The reaction mixture was diluted with EA (300 mL) and H₂O (300 mL), and stirred for 1 h. The organic layer was separated, dried, and concentrated in vacuo to get compound 2 (18 g, 94%) as yellow oil.

Step 2:

Compound 2 (1.89 g, 10 mmol), ethyl 7-bromoquinoline-3-carboxylate (1.40 g, 5 mmol), Pd₂(dba)₃ (458 mg, 0.5 mmol), Brettphos (268 mg, 0.5 mmol) and Cs₂CO₃ (4.87 g, 15 mmol) were combined in toluene (35 mL). The reaction was stirred at 85° C. under N₂ atmosphere overnight. The reaction mixture was diluted with EA (50 mL) and H₂O (50 mL), and stirred for 1 h. The organic layer was separated, dried, and concentrated in vacuo to get a residue, which was purified by silica gel column chromatography to get compound 3 (1.16 g, 60%) as yellow solid.

Step 3:

Compound 3 (3.88 g, 10 mmol) and LiOH (840 mg, 20 mmol) were combined in EtOH (10 mL). The reaction was stirred at rt overnight. HCl (2M, 40 mL) was added to the crude reaction mixture. The resulting mixture was filtered to get compound 4 (3.50 g, 97%) as yellow solid.

Step 4:

Compound 4 (360 mg, 1 mmol), tert-butyl 2-amino-4-(thiophen-2-yl)phenylcarbamate (290 mg, 1 mmol) and EDCI (573 mg, 3 mmol) were combined in Py (10 mL). The reaction was stirred at rt overnight. The reaction was diluted EA (20 mL) and H₂O (20 mL), and stirred for 1 h. The organic layer was separated, dried, and concentrated in vacuo to get a residue, which was purified by silica gel column chromatography to get compound 5 (506 mg, 80%) as yellow solid.

Step 5:

Compound 5 (316 mg, 0.5 mmol) and TFA (2 mL) were combined in DCM (5 mL). The reaction was stirred at rt for 1 h. The mixture was concentrated to get 026 (200 mg, 92%) as yellow solid. LCMS: m/z=433 (M+H)⁺. ¹H NMR (400 MHz, DMSO) δ 11.212 (s, 1H), 9.688 (s, 1H), 9.525 (s, 1H), 9.129 (s, 2H), 8.312-8.289 (d, J=9.2, 1H), 7.844 (S, 1H), 7.712 (s, 1H), 7.635-7.500 (m, 3H), 7.493-7.408 (m, 1H), 7.388-7.356 (m, 1H), 7.156-7.140 (m, 1H), 4.395-4.365 (m, 2H), 3.129-3.100 (m, 2H), 2.596-2.569 (m, 2H), 2.253-2.219 (m, 2H).

Example 23—Synthesis of Compound 027

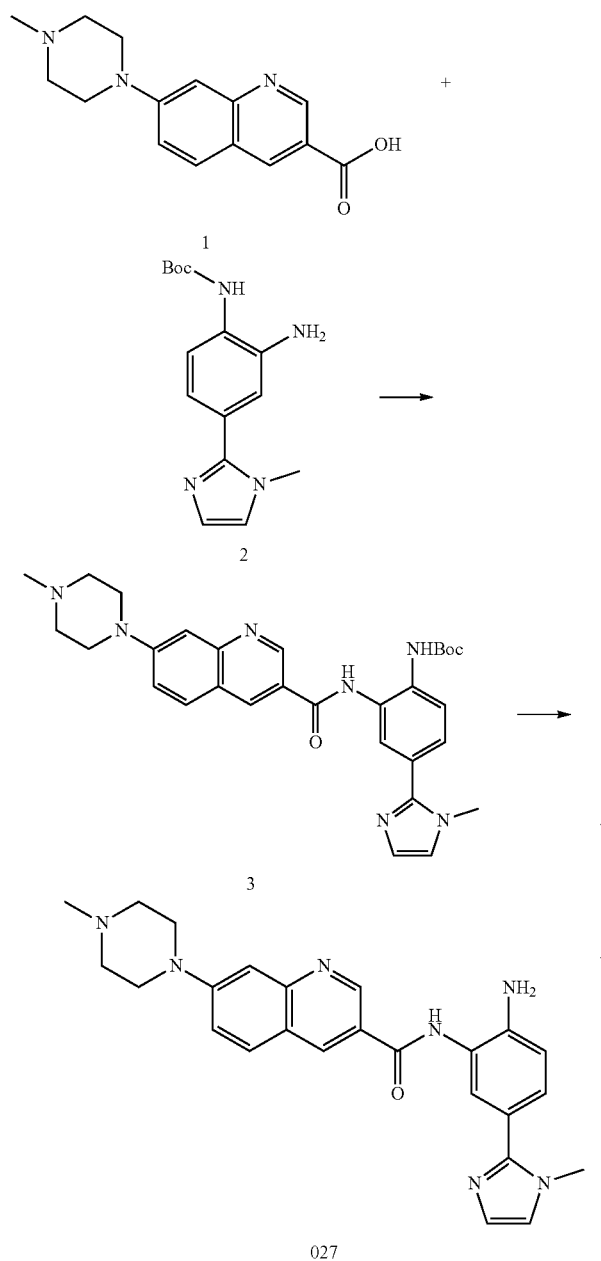

Step 1:
7-(4-Methylpiperazin-1-yl)quinoline-3-carboxylic acid (200 mg, 0.74 mmol) and EDCI (248 mg, 1.30 mmol) were dissolved in pyridine (10 mL). The reaction was stirred at rt for 20 min. tert-Butyl 2-amino-4-(1-methyl-1H-imidazol-2-yl)phenylcarbamate (230 mg, 0.80 mmol) was then added. The reaction was stirred at rt for 18 h, then concentrated in vacuo. The residue was purified by prep-TLC to give compound 3.

Step 2:
tert-Butyl 4-(1-methyl-1H-imidazol-2-yl)-2-(7-(4-methylpiperazin-1-yl)quinoline-3-carboxamido)phenylcarbamate (0.74 mmol) was dissolved in water and MeOH. HCl/dioxane (1 mL) was added at 0° C. The reaction was stirred at 0° C. to rt for 18 h, then concentrated in vacuo, and the residue was purified by prep-HPLC to give product 027 as a grey solid (30 mg). LCMS: m/z=442.2 (M+H)$^+$. $^1$H-NMR (400 MHz, DMSO) δ 9.88 (s, 1H), 9.24 (s, 1H), 8.77 (s, 1H), 7.91 (d, J=8.5, 1H), 7.57 (d, J=8.0, 1H), 7.55 (s, 1H), 7.28-7.32 (m, 2H), 7.15 (s, 1H), 6.88 (s, 1H), 6.85 (d, J=8.4, 1H), 5.31 (s, 2H), 3.71 (s, 3H), 3.42 (t, 4H), 2.25 (s, 3H).

Example 24—Synthesis of Compound 028

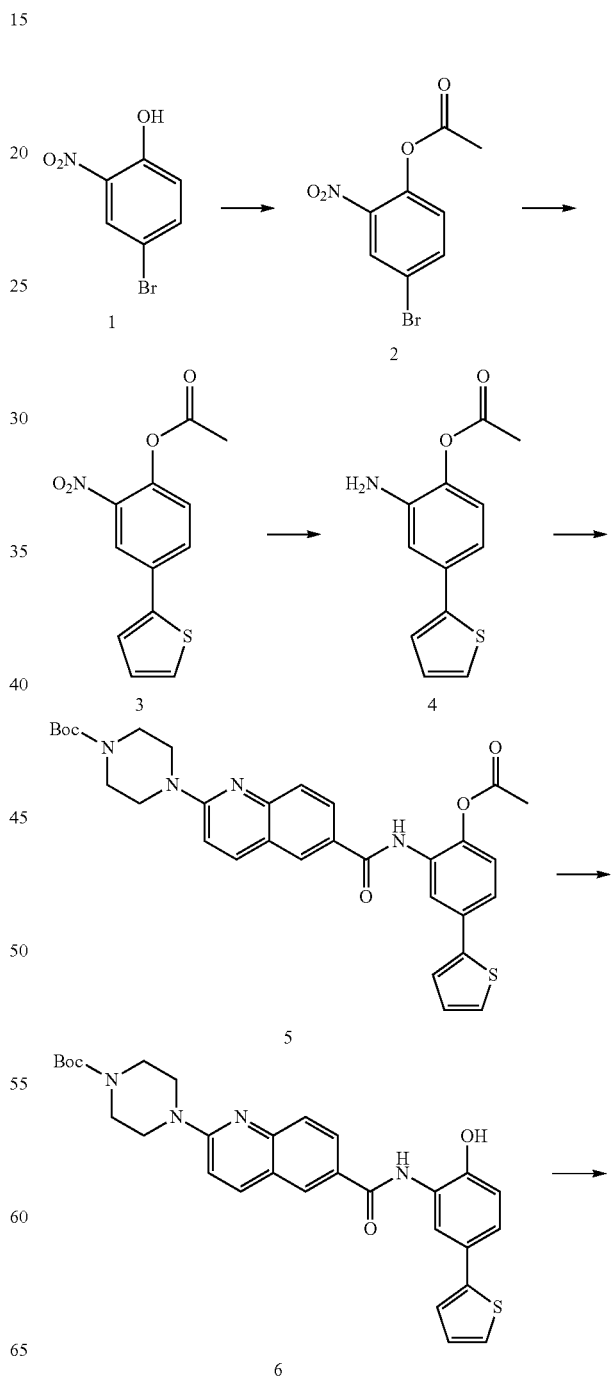

-continued

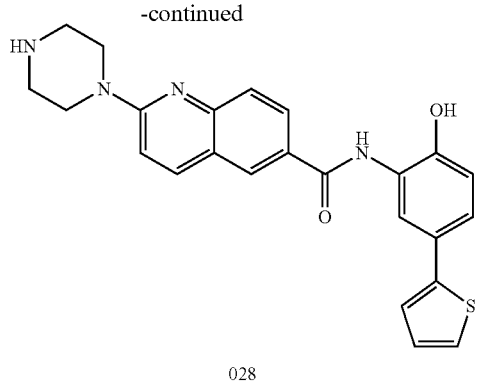

028

Step 1:
To a solution of 4-bromo-2-nitrophenol (500 mg, 2.3 mmol) in DCM (20 mL) was added Et₃N (464 mg, 4.6 mmol) and DMAP (28 mg, 0.1 mmol, cat.) followed by acetic anhydride (258 mg, 2.5 mmol). The mixture was stirred at rt overnight. After the reaction was complete, the mixture was purified by silica gel chromatography (petroleum ether/EA=3:1) to afford the compound 2 as yellow solid (576 mg, 96%)

Step 2:
Under N₂, 4-bromo-2-nitrophenyl acetate (1.8 g, 6.9 mmol) was dissolved in t-BuOH (30 mL). Thiophen-2-ylboronic acid (876 mg, 6.9 mmol), Pd₂(dba)₃ (631 mg, 0.69 mmol), Xphos (328 mg, 0.69 mmol) and K₃PO₄ (2.9 g, 14 mmol) were added. The reaction was stirred at 130° C. under microwave for 30 min. The residue was purified by column chromatography on silica gel (200-300 mesh, eluting with petroleum ether/EtOAc=3:1) to give compound 3 (485 mg, 26%).

Step 3:
To a solution of 2-nitro-4-(thiophen-2-yl)phenyl acetate (500 mg, 1.9 mmol) in EtOH (15 mL) was added Pd/C (50 mg, 10% w/w), AcOH (11 mg, 0.19 mmol, cat.). The mixture was stirred under H₂ at 60° C. for 2 h. After completed, the mixture was filtered to afford the desired amine 4 (430 mg, 97%)

Step 4:
A mixture of 2-(4-(tert-butoxycarbonyl)piperazin-1-yl) quinoline-6-carboxylic acid (357 mg, 1 mmol), compound 4 (321 mg, 0.9 mmol) and EDCI (382 mg, 2 mmol) were dissolved in pyridine (8 mL). The reaction solution was stirred at rt for 18 h, then concentrated in vacuo. The crude residue was washed with water and dried in vacuo. The residue was purified by prep-TLC to give product 5 (460 mg, crude) as a yellow oil.

Step 5:
To a solution of crude 5 (460 mg, crude) in MeOH (10 mL) was added ammonia (2 mL). The mixture was stirred at 40° C. for 2 h. After completed, the mixture was purified by prep-TLC to afford the desired product 6 (127 mg, 22%, 2 steps).

Step 6:
At 0° C., to a mixture of tert-butyl 4-(6-((2-hydroxy-5-(thiophen-2-yl)phenyl)carbamoyl)-quinolin-2-yl)piperazine-1-carboxylate (127 mg) in DCM (8 mL) was added TFA (2 mL). The reaction was stirred at 0° C. to rt for 2 h, then concentrated in vacuo. The crude residue was purified by prep-HPLC to give 028 as a white solid (12.5 mg, FA salt). LCMS: m/z=431.2 (M+H)+. 1H NMR (400 MHz, DMSO) δ 10.62 (s, 1H), 9.21 (s, 1H), 8.82 (d, J=2.0 Hz, 1H), 8.56 (s, 1H), 8.11 (d, J=9.2 Hz, 1H), 7.79 (dd, J=9.4, 2.6 Hz, 1H), 7.53 (brs, 1H), 7.47 (dd, J=5.0, 1.0 Hz, 1H), 7.32 (dd, J=3.6, 1.2 Hz, 1H), 7.29 (dd, J=8.4, 2.4 Hz, 1H), 7.11 (dd, J=5.2, 3.6 Hz, 1H), 7.00 (d, J=8.4 Hz, 1H), 3.49 (s, 4H), 3.12 (s, 4H).

Example 25—Synthesis of Compound 029

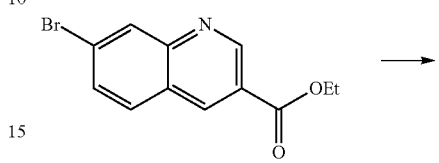

1

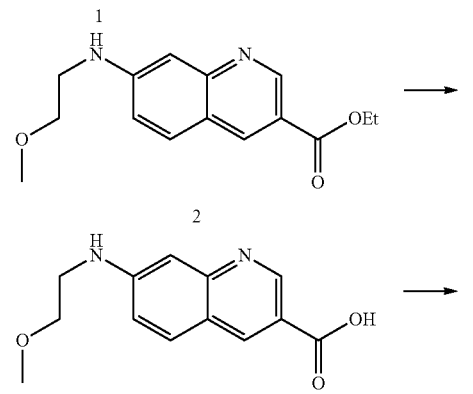

2

3

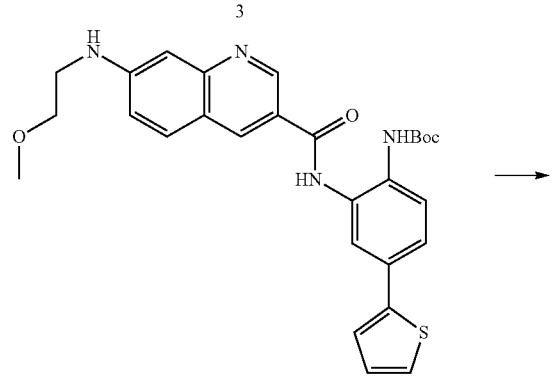

4

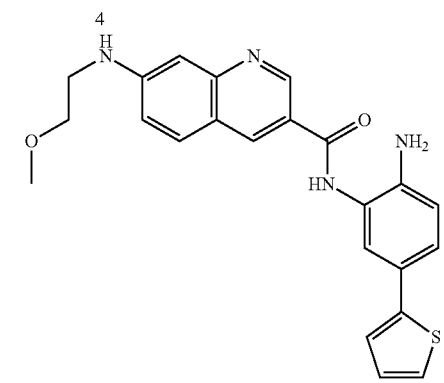

029

Step 1:
Under N₂, ethyl 7-bromoquinoline-3-carboxylate (500 mg, 1.78 mmol), 2-methoxy-ethanamine (134 mg, 1.78 mmol), tris(dibenzylideneacetone) dipalladium (41 mg, 0.045 mmol), Ruphos (42 mg, 0.089 mmol) and Cs₂CO₃ (1.16 g, 3.57 mmol) were combined in toluene (15 mL). The reaction was heated to 100° C. and stirred for 18 h. The reaction was cooled to rt. and filtered. The filtrate was concentrated in vacuo, and the residue was purified by prep-TLC to give compound 2 (288 mg, 47%).

Step 2:

Ethyl 7-(2-methoxyethylamino)quinoline-3-carboxylate (288 mg, 1.05 mmol) and LiOH (133 mg, 3.15 mmol) were combined in THF (8 mL), water (2.6 mL) and MeOH (1.3 mL). The reaction was stirred at rt until the reaction was complete. MeOH and THF were then removed in vacuo, and the aqueous phase was adjusted to pH 7. The aqueous phase was then concentrated in vacuo to give crude 3.

Step 3:

7-(2-Methoxyethylamino)quinoline-3-carboxylic acid (240 mg, 0.97 mmol), tert-butyl 2-amino-4-(thiophen-2-yl) phenyl carbamate (160 mg, 0.55 mmol) and EDCI (380 mg, 1.98 mmol) were combined in pyridine (12 mL). The residue was washed with water, purified by column chromatography on silica gel (200-300 mesh, eluting with petroleum ether/EtOAc=1:2) to give compound 4 as a yellow solid (300 mg, yield: 67%).

Step 4:

tert-Butyl 2-(7-(2-methoxyethylamino)quinoline-3-carboxamido)-4-(thiophen-2-yl)phenylcarbamate (300 mg, 0.58 mmol) was dissolved in DCM (4 mL). TFA (3 mL) was added at 0° C. and the reaction stirred at 0° C. to rt for 2 h. The reaction was concentrated in vacuo and the residue was purified by prep-HPLC to give product 029 as a yellow solid (120.4 mg, 50%). LCMS: m/z=419.1 (M+H)⁺. ¹H-NMR (400 MHz, DMSO) δ 9.84 (s, 1H), 9.21 (s, 1H), 8.74 (s, 1H), 7.88 (d, J=8.5, 1H), 7.53 (s, 1H), 7.38 (d, J=8.0, 2H), 7.32 (d, J=8.5, 1H), 7.26 (s, 1H), 7.06 (s, 2H), 6.84 (d, J=8.5, 1H), 5.21 (s, 2H), 3.59 (t, 2H), 3.37 (t, 2H), 3.31 (s, 3H).

Example 26—Synthesis of Compound 030

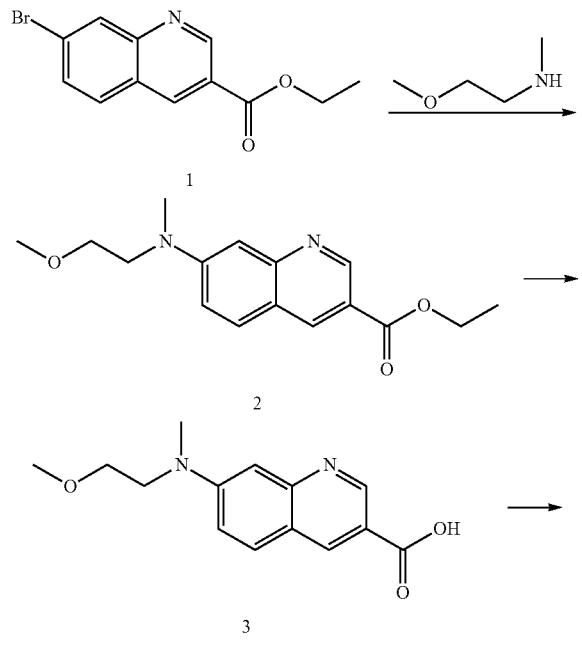

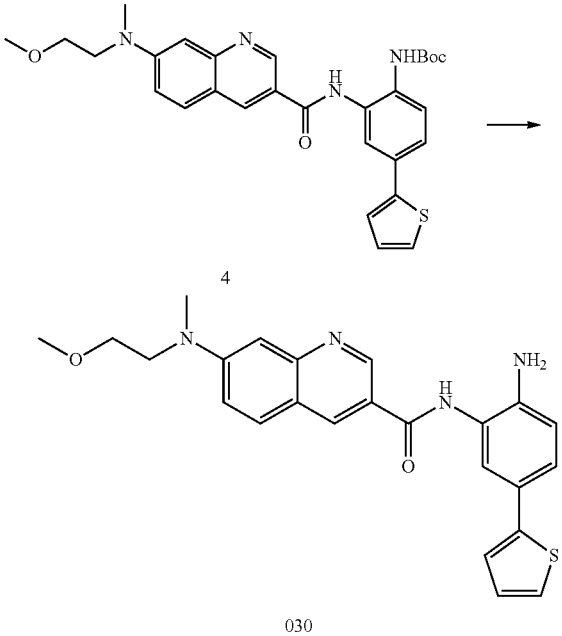

Step 1:

Under N₂, ethyl 7-bromoquinoline-3-carboxylate (280 mg, 1 mmol), 2-methoxy-N-methylethanamine (89 mg, 1 mmol), Pd₂(dba)₃ (92 mg, 0.1 mmol), Ruphos (93 mg, 0.2 mmol) and Cs₂CO₃ (652 mg, 2 mmol) were combined in toluene (10 mL). The reaction was stirred at 100° C. overnight. The residue was purified by column chromatography on silica gel (200-300 mesh, eluting with petroleum ether/EtOAc=1:2) to give compound 2 (250 mg, 89%).

Step 2:

Ethyl 7-((2-methoxyethyl)(methyl) amino) quinoline-3-carboxylate (250 mg, 0.87 mmol) and LiOH (55 mg, 1.3 mmol) were combined in EtOH (4 mL) and water (0.5 mL). The reaction was stirred at 60° C. for 4 h, then concentrated in vacuo to remove EtOH. The aqueous phase was adjusted to pH 7, then it was concentrated in vacuo to give the compound 3 (200 mg, 89%).

Step 3:

7-((2-Methoxyethyl)(methyl) amino) quinoline-3-carboxylic acid (200 mg, 0.77 mmol), tert-butyl (2-amino-4-(thiophen-2-yl)phenyl)carbamate (223 mg, 0.77 mmol) and EDCI (444 mg, 2.31 mmol) were dissolved in pyridine (5 mL). The reaction was stirred at rt overnight. The reaction was then concentrated in vacuo, and the crude material was purified by column chromatography on silica gel (200-300 mesh, eluting DCM/CH₃OH=1:1) to give compound 4 (300 mg, 76%).

Step 4:

tert-Butyl 2-(7-((2-methoxyethyl)(methyl) amino) quinoline-3-carboxamido)-4-(thiophen-2-yl) phenylcarbamate (300 mg, 0.56 mmol) and TFA (2 mL) were combined in DCM (4 mL). The reaction was stirred at rt for 2 h, then concentrated in vacuo. The crude material was washed with diethyl ether, and purified by prep-TLC (DCM/CH3OH=1:1) to give the product 030 (70 mg, 29%). LCMS: m/z=433.1 (M+H)⁺. ¹H-NMR (500 MHz, DMSO) δ 9.84 (s, 1H), 9.21 (s, 1H), 8.74 (s, 1H), 7.88 (d, J=8.5, 1H), 7.53 (s, 1H), 7.38 (d, J=8.0, 2H), 7.32 (d, J=8.5, 1H), 7.26 (s, 1H), 7.06 (s, 2H), 6.84 (d, J=8.5, 1H), 5.24 (s, 2H), 3.72 (s, 2H), 3.59 (s, 2H), 3.31 (s, 3H), 3.12 (s, 3H).

Example 27—Synthesis of Compound 031

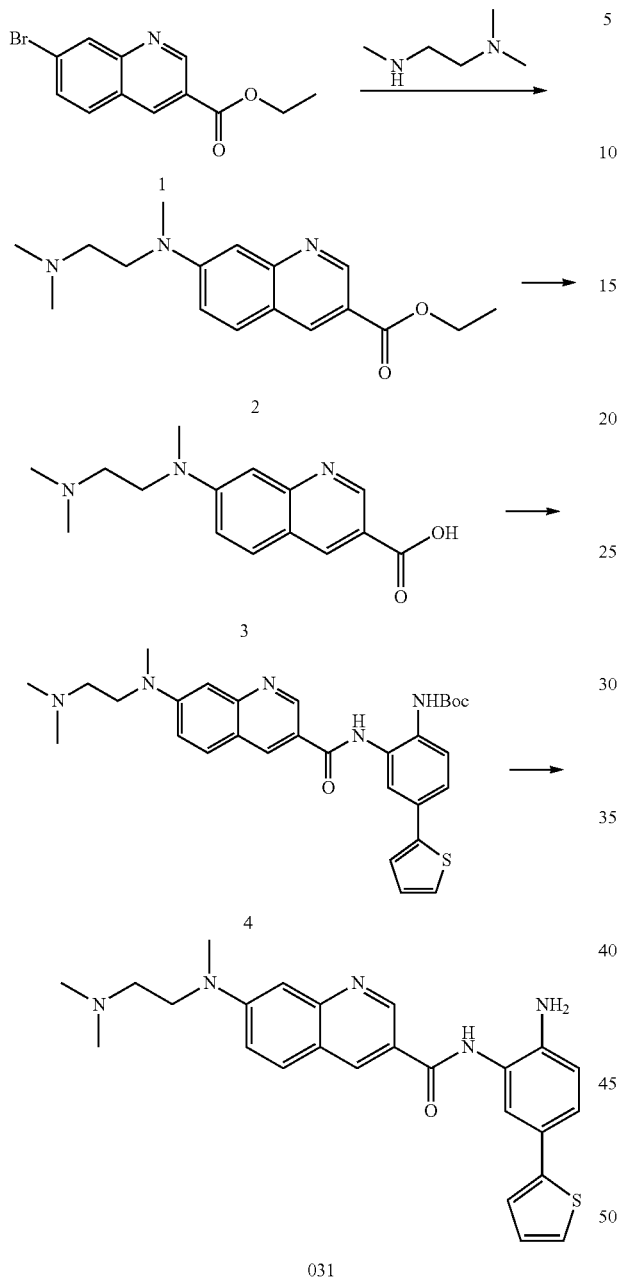

Step 1:

Under $N_2$, ethyl 7-bromoquinoline-3-carboxylate (500 mg, 1.79 mmol), $N_1,N_1,N_2$-trimethylethane-1,2-diamine (182 mg, 1.79 mmol), Pd(OAc)$_2$ (40 mg, 0.18 mmol), Xphos (172 mg, 0.36 mmol) and Cs$_2$CO$_3$ (1174 mg, 3.6 mmol) were combined in toluene (10 mL). The reaction was stirred at 100° C. overnight. The residue was purified by column chromatography on silica gel (200-300 mesh, eluting with petroleum ether/EtOAc=1:2) to give the compound 2 (280 mg, crude).

Step 2:

Ethyl 7-((2-(dimethylamino) ethyl)(methyl) amino) quinoline-3-carboxylate (280 mg, 0.93 mmol) and LiOH (59 mg, 1.4 mmol) were combined in EtOH (4 mL) and water (0.5 mL), and the reaction was stirred at 60° C. for 4 h. The reaction was concentrated in vacuo. The aqueous phase was adjusted to pH 7, then concentrated in vacuo to give the compound 3 (280 mg, crude).

Step 3:

7-((2-(Dimethylamino) ethyl)(methyl) amino) quinoline-3-carboxylic acid (280 mg, 1 mmol), tert-butyl (2-amino-4-(thiophen-2-yl)phenyl)carbamate (232 mg, 0.8 mmol), and EDCI (576 mg, 3 mmol) were dissolved in pyridine (5 mL) and stirred at rt overnight. The reaction was then concentrated in vacuo and the crude material was carried over for next step (400 mg, crude).

Step 4:

tert-Butyl 2-(7-((2-(dimethylamino) ethyl)(methyl) amino) quinoline-3-carboxamido)-4-(thiophen-2-yl) phenylcarbamate (400 mg, 0.73 mmol) and TFA (2 mL) were combined in DCM (4 mL), and the reaction was stirred at rt for 2 h. The reaction was then concentrated in vacuo and purified by prep-HPLC (base method) to give the product 031 (57 mg, 18%). LCMS: m/z=446.1 (M+H)$^+$. $^1$H-NMR (500 MHz, DMSO) δ 9.88 (s, 1H), 9.22 (s, 1H), 8.75 (s, 1H), 8.26 (s, 1H), 7.90 (d, J=9.0, 1H), 7.53 (d, J=2.0, 1H), 7.31-7.36 (m, 3H), 7.26 (d, J=3.0, 1H), 7.06 (t, 2H), 6.84 (d, J=8.5, 1H), 3.69 (t, J=6.5, 2H), 3.11 (s, 3H), 2.66 (t, J=6.5, 2H), 2.37 (s, 6H).

Example 28—Synthesis of Compound 032

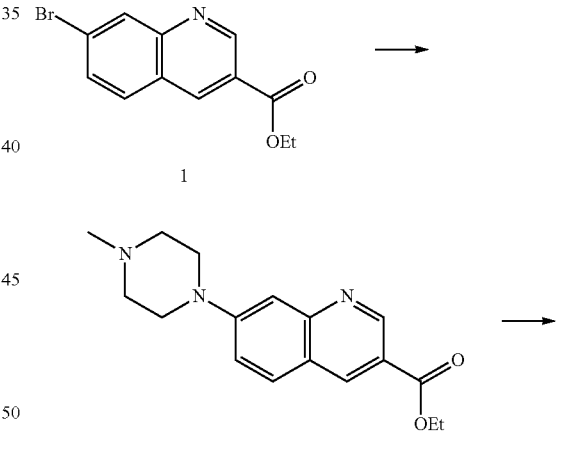

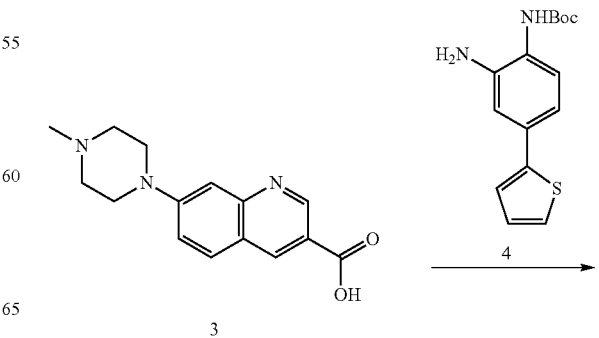

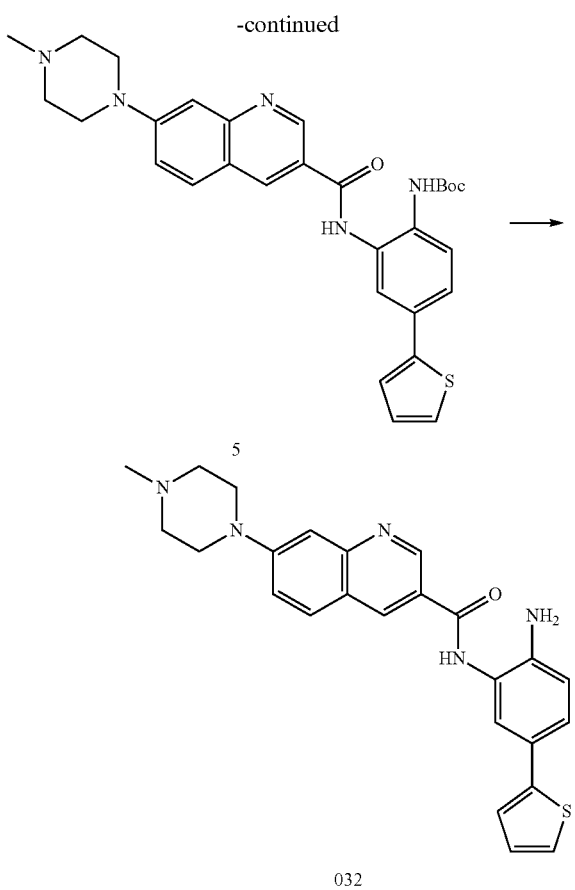

Step 1:
Under N₂, Ethyl 7-bromoquinoline-3-carboxylate (1.1 g, 3.93 mmol), 1-methylpiperazine (432 mg, 4.31 mmol), Pd$_2$(dba)$_3$ (89 mg, 0.097 mmol), Ruphos (91 mg, 0.195 mmol) and Cs$_2$CO$_3$ (2.563 g, 7.87 mmol) were combined in toluene (53 mL) and stirred at 100° C. for 18 h. The crude material was purified by column chromatography on silica gel (200-300 mesh, eluting with petroleum ether/EtOAc=1:2) to give the compound 2 (1.1 g, 93.6%).

Step 2:
Ethyl 7-(4-methylpiperazin-1-yl)quinoline-3-carboxylate (1.1 g, 3.67 mmol) and LiOH (463 mg, 11.02 mmol) were combined in THF (23 mL), MeOH (3.8 mL) and water (7.6 mL). The reaction was stirred at rt for 4 h, then concentrated in vacuo to remove THF and MeOH. The aqueous phase was adjusted to pH 7, then concentrated in vacuo to give the compound 3 (2 g, crude).

Step 3:
7-(4-Methylpiperazin-1-yl)quinoline-3-carboxylic acid (1.065 g, crude), tert-butyl (2-amino-4-(thiophen-2-yl)phenyl)carbamate (484 mg, 1.67 mmol) and EDCI (750 mg, 3.91 mmol) were dissolved in pyridine (19 mL) and stirred at rt overnight. The reaction was concentrated in vacuo, and the crude residue was purified by column chromatography on silica gel (200-300 mesh, eluting DCM/CH$_3$OH=1:1) to give compound 5 (1.9 g, crude).

Step 4:
tert-Butyl (2-(7-(4-methylpiperazin-1-yl)quinoline-3-carboxamido)-4-(thiophen-2-yl)phenyl)carbamate (1.9 g, crude) and TFA (5 mL) were combined in DCM (5 mL). The reaction was stirred at rt for 1 h then concentrated in vacuo. The crude material was washed with diethyl ether, and the residue was purified by prep-HPLC (0.1% NaHCO$_3$/water-acetonitrile) to give the product 032 (365 mg, 45.6%).

LCMS: m/z=444 (M+H)⁺. ¹H-NMR (400 MHz, DMSO) δ 9.84 (s, 1H), 9.21 (s, 1H), 8.74 (s, 1H), 7.88 (d, J=8.5, 1H), 7.53 (s, 1H), 7.38 (d, J=8.0, 2H), 7.32 (d, J=8.5, 1H), 7.26 (s, 1H), 7.06 (s, 2H), 6.84 (d, J=8.5, 1H), 5.25 (s, 2H), 3.41 (t, 4H), 2.50 (t, 4H), 2.25 (s, 3H).

Example 29—Pharmacokinetics

Male SD rats were fasted overnight. Compounds of the invention were dissolved in dimethyl acetamide at 10 times the final concentration, then Solutol HS 15 (BASF) was added to a final concentration of 10%. Finally, 80% saline was added and vortexed to achieve a clear solution. For the IV dosing three animals were injected via the foot dorsal vein with 1 mg/kg compound. For the PO dosing 5 mg/kg of compound was delivered by oral gavage. Blood was collected via the tail vein into K2EDTA tubes at 5 minutes, 15 minutes, 30 minutes, 1 hour, 2 hours, 4 hours, 8 hours and 24 hours after dosing. The blood was centrifuged at 2000 g for 5 minutes at 4° C. to obtain plasma. The plasma was extracted with acetonitrile and the level of compound was analyzed by LC/MS/MS. The level of compound in plasma was calculated from a standard curve in rat plasma. The IV clearance (L/h/kg) and area under the curve (h*ng/mL) were calculated using WinNonLin software. The dose adjusted area under the curve for the IV and oral dosing were used to calculate the oral bioavailability.

Pharmacokinetic properties were assessed in a rat cassette dosing experiment. The IV clearance (IV Clr.) is in units of L/hr/kg. The oral maximum plasma concentration (PO Cmax) is in units of ng/ml. The oral plasma half-life (PO T½) is in units of hours. The oral area under the curve (PO AUC) is in units of hours*ng/ml. The fraction absorbed by the oral route (F %) is a percentage of the oral area under the curve to the IV area under the curve, dose adjusted. A summary of results is presented in Table 3 and Table 4, below.

TABLE 3

PK Parameters (Rat IV)

| Compound | IV Clr. (L/h/kg) | IV t$_{1/2}$ (h) | IV AUC (h*ng/mL) |
|---|---|---|---|
| 001 | | | 40050-40150 |
| 002 | 0.01-0.5 | 1-5 | 6500-6600 |
| 003 | 0.1-1 | 5-10 | 1800-1900 |
| 004 | 0.01-0.5 | 15-20 | 10650-10750 |
| 009 | 0.01-0.5 | 15-20 | 10750-10850 |
| 011 | 0.1-1 | 5-10 | 2000-2100 |
| 012 | 0.01-0.5 | 5-10 | 29850-29950 |
| 013 | 0.1-1 | 1-5 | 2700-2800 |
| 018 | 0.01-0.5 | 10-15 | 19650-19750 |
| 021 | 0.1-1 | 1-5 | 3700-3800 |
| 024 | 0-0.5 | 15-20 | 20-25 |
| 025 | 0-0.5 | 1-5 | 15-20 |
| 029 | 0-0.1 | 1-3 | 20-25 |
| 030 | 0-0.1 | 0-0.5 | 1-5 |
| 031 | 0-0.2 | 0.5-1 | 1-5 |
| 032 | 0-0.5 | 0.5-2 | 0-15 |

TABLE 4

PK Parameters (Rat PO)

| Compound | C$_{max}$ | PO t$_{1/2}$ (h) | PO AUC (h*ng/mL) | F % |
|---|---|---|---|---|
| 001 | 6950-7000 | | 139950-140050 | 65-75 |
| 002 | 2450-2500 | 5-10 | 22350-22450 | 65-75 |
| 003 | 950-1000 | 5-10 | 11450-11550 | 130-140 |

TABLE 4-continued

| | PK Parameters (Rat PO) | | | |
|---|---|---|---|---|
| Compound | $C_{max}$ | PO $t_{1/2}$ (h) | PO AUC (h*ng/mL) | F % |
| 004 | 3500-3550 | 10-15 | 61250-61350 | 110-115 |
| 009 | 4150-4200 | 10-15 | 65250-65350 | 115-125 |
| 011 | 700-750 | 5-10 | 8000-8100 | 80-90 |
| 012 | 8200-8250 | 15-20 | 9450-9550 | 60-70 |
| 013 | 1900-1950 | 1-5 | 11750-11850 | 80-90 |
| 018 | 5550-5600 | 5-10 | 81850-81950 | 75-85 |
| 021 | 5250-5300 | 1-5 | 21350-21450 | 110-120 |

Example 21—HDAC Enzyme Assays

Compounds for testing were diluted in DM30 to 50 fold the final concentration and a ten-point three-fold dilution series was made. The compounds were diluted in assay buffer (50 mM HEPES, pH 7.4, 100 mM KCl, 0.001% Tween-20, 0.05% BSA, 20 μM TCEP) to 6-fold their final concentration. The HDAC enzymes (purchased from BPS Biosciences) were diluted to 1.5-fold their final concentration in assay buffer. The tripeptide substrate and trypsin at 0.05 μM final concentration were diluted in assay buffer at 6-fold their final concentration. The final enzyme concentrations used in these assays were 3.3 ng/ml (HDAC1), 0.2 ng/ml (HDAC2) and 0.08 ng/ml (HDAC3). The final substrate concentrations used were 16 μM (HDAC1), 10 μM (HDAC2) and 17 μM (HDAC3).

Five μl of compounds and 20 μl of enzyme were added to wells of a black, opaque 384 well plate in duplicate. Enzyme and compound were incubated together at room temperature for 10 minutes. Five μl of substrate was added to each well, the plate was shaken for 60 seconds and placed into a Victor 2 microtiter plate reader. The development of fluorescence was monitored for 60 min and the linear rate of the reaction was calculated. The $IC_{50}$ was determined using Graph Pad Prism by a four parameter curve fit.

TABLE 5

| | $IC_{50}$ (nM) | | |
|---|---|---|---|
| Compound | HDAC1 | HDAC2 | HDAC3 |
| 001 | 5-10 | 10-15 | 340-350 |
| 002 | 20-25 | 45-50 | 925-935 |
| 003 | 1-10 | 5-25 | 145-590 |
| 004 | 5-10 | 25-30 | 530-540 |
| 006 | 10-15 | 70-75 | 1130-1140 |
| 007 | 25-35 | 60-65 | 2740-2750 |
| 008 | 625-650 | >2000 | >2000 |
| 009 | 10-15 | 40-45 | 470-480 |
| 010 | 375-380 | 210-220 | 985-995 |
| 011 | 10-15 | 35-40 | 490-500 |
| 012 | 25-35 | 20-30 | 875-885 |
| 013 | 25-35 | 70-80 | 1040-1050 |
| 014 | 4185-4195 | 2140-2150 | 3370-3380 |
| 015 | 15-25 | 30-40 | 640-650 |
| 016 | 1-10 | 5-15 | 710-720 |
| 017 | 1-10 | 10-20 | 450-460 |
| 018 | 1-10 | 20-35 | 150-235 |
| 019 | 15-20 | 35-40 | 690-700 |
| 020 | 5-10 | 25-30 | 1300-1310 |
| 021 | 5-10 | 15-20 | 430-440 |
| 022 | 885-895 | 1240-1250 | 1210-1220 |
| 024 | 0-5 | 5-10 | 15-90 |
| 025 | 5-15 | 15-20 | 110-120 |
| 026 | 25-30 | 20-25 | 85-95 |
| 027 | >2000 | >2000 | >2000 |
| 028 | 50-60 | 50-60 | 290-300 |
| 029 | 15-25 | 50-105 | 750-760 |

TABLE 5-continued

| | $IC_{50}$ (nM) | | |
|---|---|---|---|
| Compound | HDAC1 | HDAC2 | HDAC3 |
| 030 | 50-55 | 155-160 | 1200-1230 |
| 031 | 0-5 | 15-25 | 240-250 |
| 032 | 5-10 | 25-35 | 280-300 |

The disclosed subject matter is not to be limited in scope by the specific embodiments and examples described herein. Indeed, various modifications of the disclosure in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes. Other embodiments are within the following claims.

The invention claimed is:

1. A compound of Formula I:

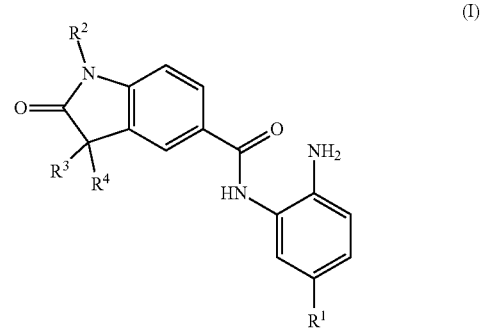

or a pharmaceutically acceptable salt thereof;
wherein:

$R^1$ is selected from the group consisting of aryl or heteroaryl, wherein aryl or heteroaryl are optionally substituted with —OH or —OSO$_2$NHCH$_3$;

$R^2$ is selected from the group consisting of —H, $C_1$-$C_6$ alkyl, alkyl-cycloalkyl, alkyl-aryl, alkyl-heteroaryl, aryl, heteroaryl, and halo; and $R^3$ and $R^4$ are independently, at each occurrence, selected from the group consisting of —H, halo, alkyl, aryl, heteroaryl, cycloalkyl, and heterocycloalkyl.

2. The compound of claim 1, wherein:

$R^1$ is selected from the group consisting of phenyl, phenyl-OH, phenyl-OSO$_2$NHMe, thienyl, and furanyl;

$R^2$ is selected from the group consisting of —H, methyl, —CH$_2$-cyclopropyl; and $R^3$ and $R^4$ are independently, at each occurrence, selected from the group consisting of of —H, halo, and methyl.

3. A compound of Formula II:

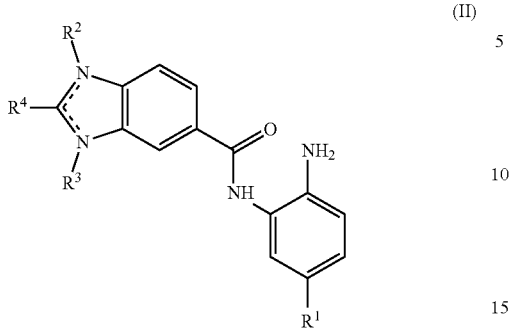

(II)

or a pharmaceutically acceptable salt thereof;

wherein:

R¹ is selected from the group consisting of aryl and heteroaryl, wherein aryl or heteroaryl are optionally substituted with —OH or —OSO₂NHCH₃;

R² is selected from the group consisting of absent, alkyl-cycloalkyl, alkyl-heterocycloalkyl, aryl, and heteroaryl;

R³ is selected from the group consisting of absent, alkyl-cycloalkyl, alkyl-heterocycloalkyl, aryl, and heteroaryl;

R⁴ is selected from the group consisting of —H, —OH, alkyl, aryl, cycloalkyl, and heteroaryl; and ------ indicates an optional double bond.

4. The compound of claim 3, wherein:

R¹ is phenyl or thienyl;

R² is absent, or C₂-alkyl-5-6 membered heterocycloalkyl;

R³ is absent, or —C₂-alkyl-5-6 membered heterocycloalkyl; and

R⁴ is selected from the group consisting of —H, cyclopropyl, and methyl.

5. The compound selected from the group consisting of:

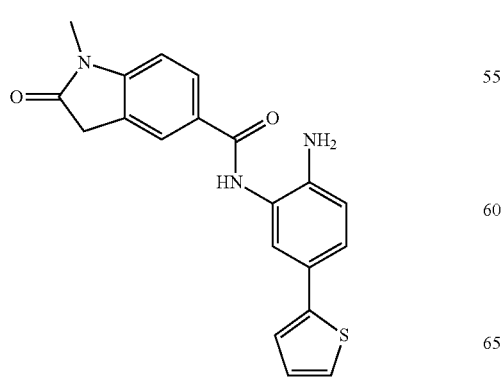

-continued

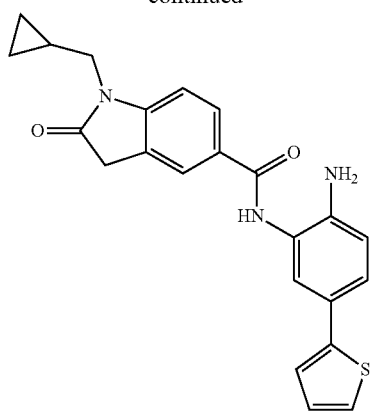

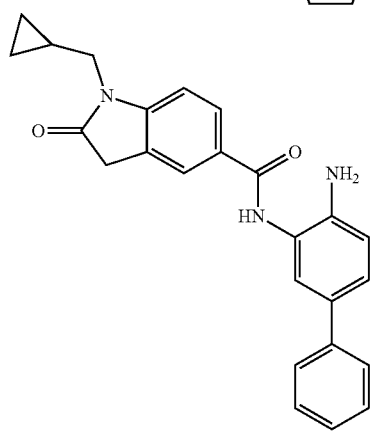

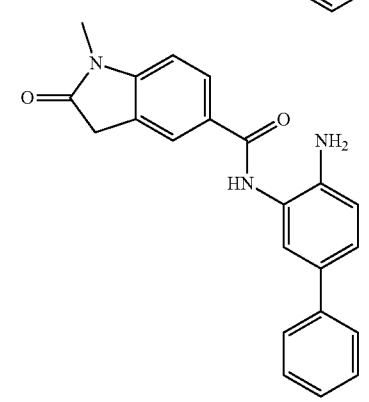

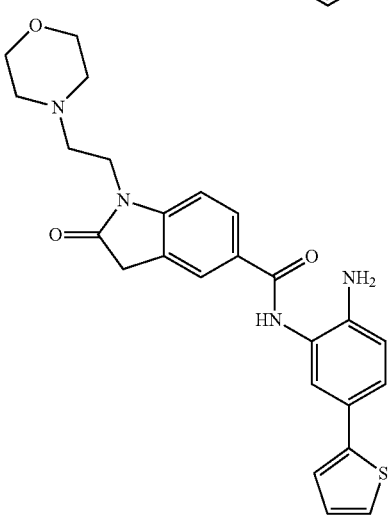

69
-continued
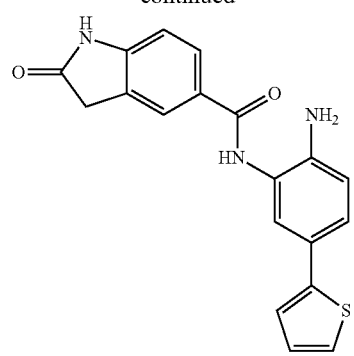
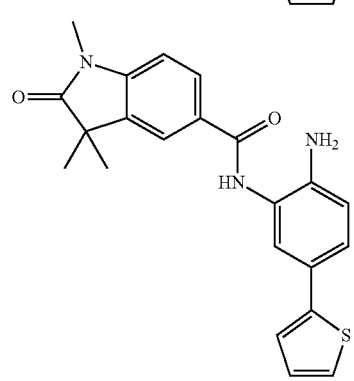
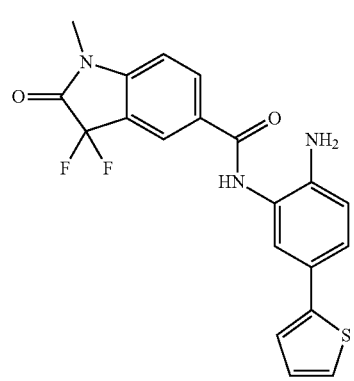
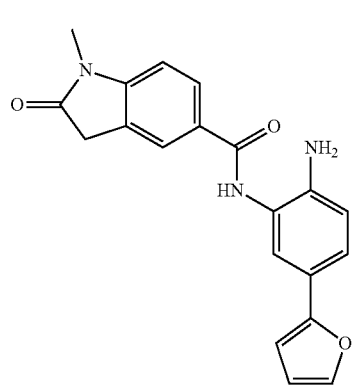
70
-continued
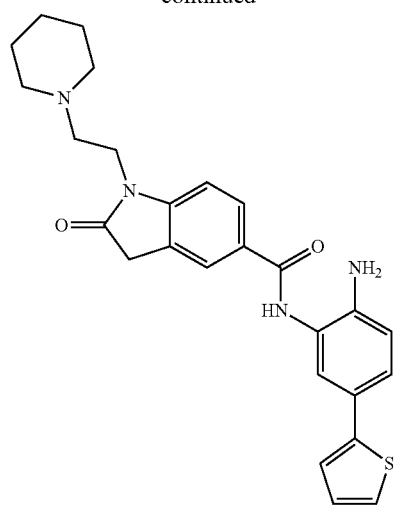
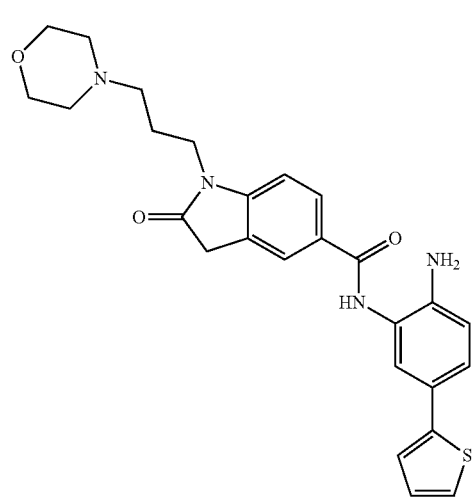
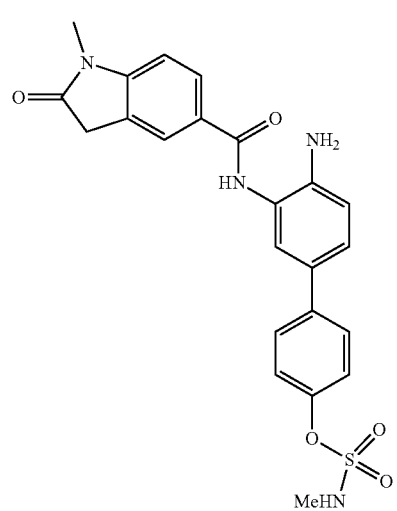

-continued
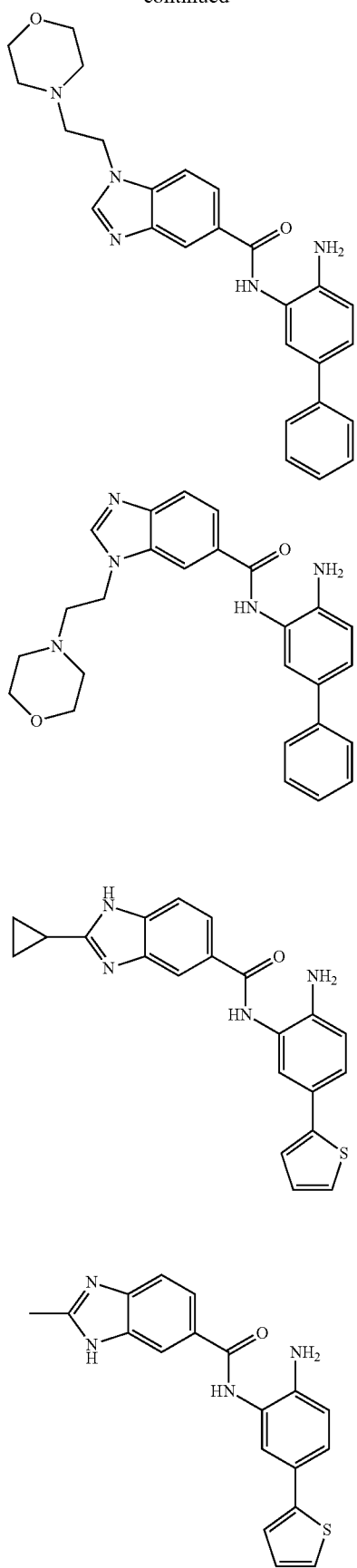
-continued
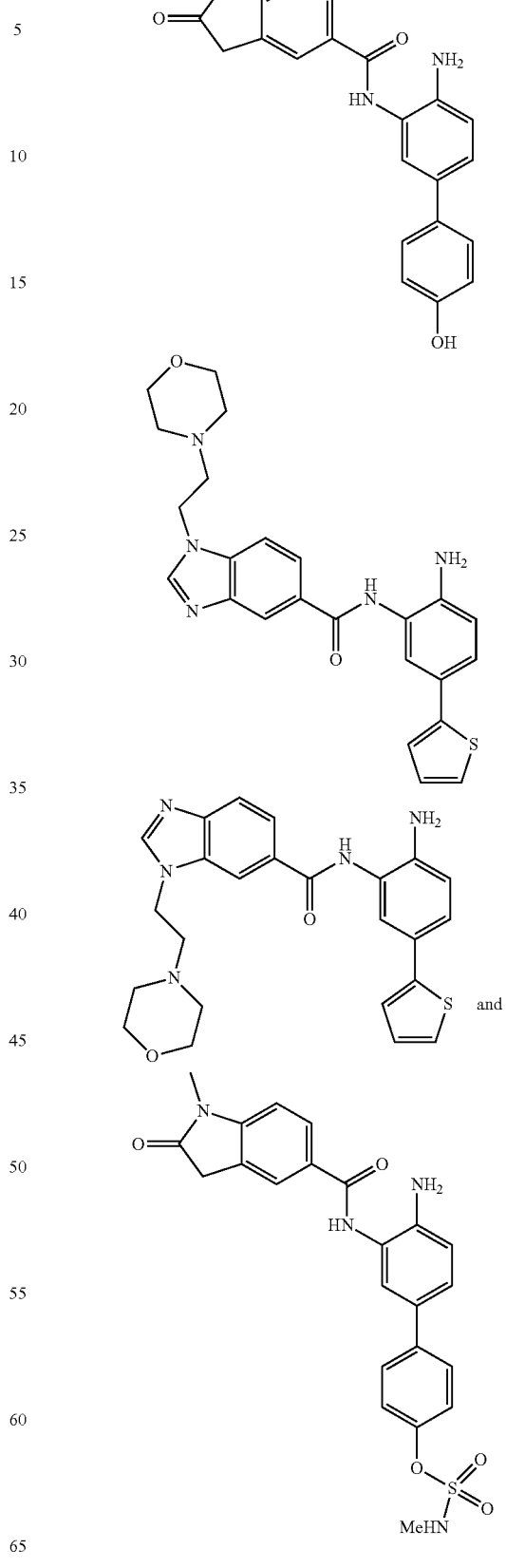
or a pharmaceutically acceptable salt thereof.

6. A compound selected from the group consisting of:

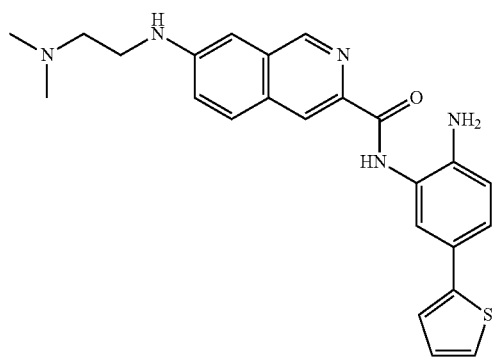

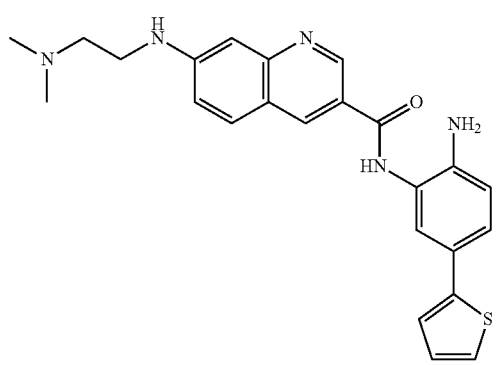

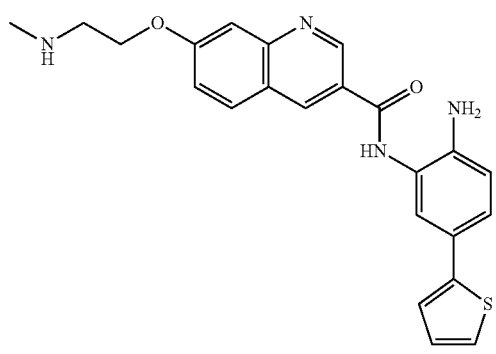

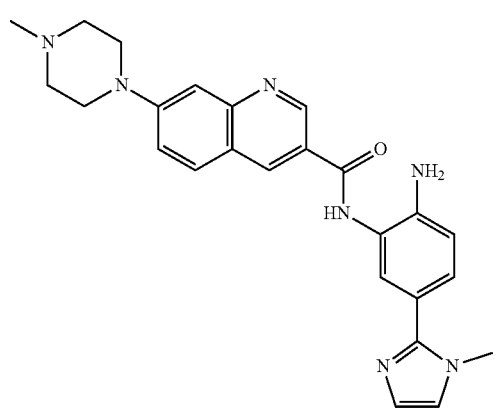

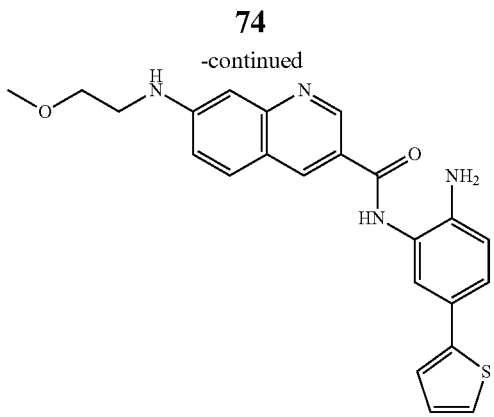

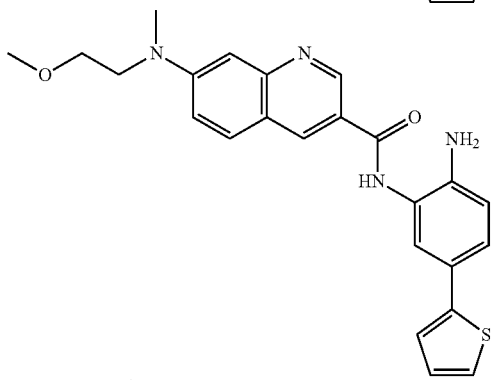

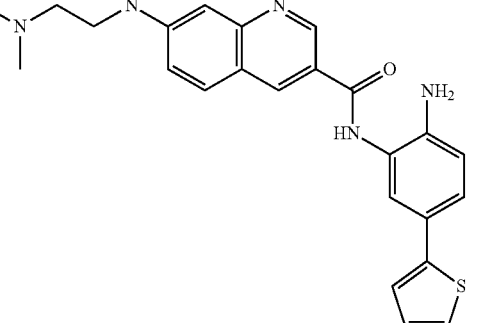

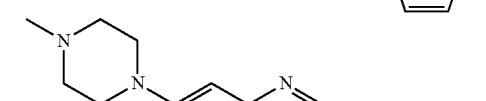 and

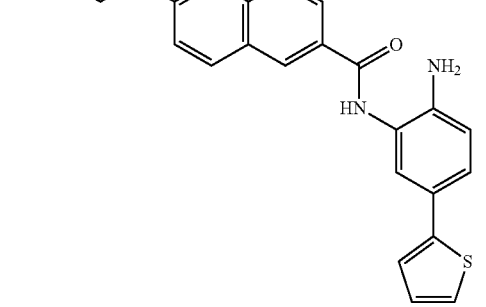

or a pharmaceutically acceptable salt thereof.

7. A pharmaceutical composition comprising a compound of claim 1, or a pharmaceutically acceptable salt thereof, together with a pharmaceutically acceptable carrier.

8. A method of inhibiting the activity of HDAC1 and/or HDAC2 in a subject of need thereof, comprising administering to the subject a therapeutically effective amount of a compound of claim 1.

9. A method of treating a disease mediated by HDAC1 and/or HDAC2 in a subject of need thereof, comprising administering to the subject a therapeutically effective amount of a compound of claim 1 wherein the disease is selected from the group consisting of a myelodysplastic syndrome, a hemoglobinopathy, alopecia, spinal muscular atrophy, inflammatory bowel disease, Crohn's ulcerative colitis, and hearing loss.

10. The method of claim 9, wherein the disease is a myelodysplastic syndrome.

11. The method of claim 9, wherein the hemoglobinopathy is a sickle-cell disease or beta-thalassemia.

12. The method of claim 9, wherein the disease is hearing loss.

13. A method of treating cancer in a subject of need thereof, comprising administering to the subject a therapeutically effective amount of a compound of claim 1, wherein the cancer is selected from the group consisting of lung cancer, colon cancer, breast cancer, neuroblastoma, leukemia, and lymphoma.

14. The method of claim 13, wherein the cancer is acute myelogenous leukemia or acute megakaryocytic leukemia.

15. The method of claim 13, wherein the cancer is neuroblastoma.

16. A method of treating diabetes in a subject of need thereof, comprising administering to the subject a therapeutically effective amount of a compound of claim 1.

* * * * *